US005849520A

United States Patent [19]
Leonard et al.

[11] Patent Number: 5,849,520

[45] Date of Patent: Dec. 15, 1998

[54] POST TRANSCRIPTIONAL GENE REGULATION BY SELENIUM

[75] Inventors: Jack L. Leonard, Shrewsbury; Peter E. Newburger, Waban, both of Mass.

[73] Assignee: University of Massachusetts Medical Center, Worcester, Mass.

[21] Appl. No.: 454,028

[22] Filed: May 30, 1995

Related U.S. Application Data

[63] Continuation-in-part of Ser. No. 66,680, May 24, 1993, abandoned.

[51] Int. Cl.[6] .......... C12P 21/06

[52] U.S. Cl. .......... 435/69.1; 435/71.1; 435/172.3; 435/357; 435/358; 435/365; 536/23.4

[58] Field of Search .......... 435/69.1, 172.1, 435/320.1, 71.1, 172.3, 358, 357, 365; 536/24.1, 23.1, 23.4, 24.5; 935/23, 44, 84

[56] References Cited

U.S. PATENT DOCUMENTS 5,272,078 12/1993 Larsen et al. .......... 435/189

FOREIGN PATENT DOCUMENTS

WO 92/13077 8/1992 WIPO .......... C12N 15/53

OTHER PUBLICATIONS

Houdebine, L.M. 1994 J. Biotechnology pp. 269–287.

Wall, R.S. 1996. Theriogenology vol. 45. pp. 57–68.

Chang et al., "Active transcription of the selenium–dependent glutathione peroxidase gene in selenium–deficient rats", Biochem. Biophys. Res. Commun., 181(3):1431–1436, Dec. 1991.

Shen et al., "Sequences in the 3'–Untranslated Region of the Human . . . Sufficient for Selenocysteine Incorporation at the UGA Codon", *The Journal of Biological Chemistry*, 268:11463–11469, (1993).

Copy of PCT Search Report for PCT/US96/07496. (The references cited were not considered, no copies were furnished).

Alberts, *Molecular Biology of the Cell*, pp. 179–180 (1983).

Baron et al., Abstract, p. 38, The Fifth Int'l Symp. on Selenium in Biology in Biology & Medicine, Jul. 20–23, 1992, Vanderbilt University School of Medicine, Nashville, TN.

Berg et al., *J. of Biological Chemistry*, 266:22386–22391, (1992).

Berry et al., Abstract, p. 2, the Fifth Int'l Symp. on Selenium in Bio. & Medicine, Jul. 20–23, 1992 Vanderbilt University School of Medicine, Nashville, TN.

Berry et al., Abstract, p. 39, The Fifth Int'l Symp. on Selenium in Bio. & Medicine, Jul. 20–23, 1992 Vanderbilt University School of Medicine, Nashville, TN.

Berry et al., *Nature*, 349:438–440, (1991).

Berry et al., *Nature*, 353;273–276, (1991).

Berry et al., *Endocrinology*, 131:1848–1852, (1992).

Böck, Abstract, p. 3, The Fifth Int'l Symp. on Selenium on Bio. and Medicine, Jul. 20–23, 1992, Vanderbilt University School of Medicine, Nashville, TN.

Böck et al., *TIBS*, 16:463–467, (1991).

Burk, *Essential and Toxic Trace Elements in Human Health and Disease:An Update*, Wiley–Liss, Inc., pp. 181–190, (1993).

Chada et al., *Genomics*, 6:268–271, (1990).

Chada et al., *Blood*, 74:2535–2541, (1989).

Chada et al., *Oxy–Radicals in Molecular Biology and Pathology*, pp. 273–288 Alan R. Liss, Inc. (1988).

Chambers et al., *The EMBO Journal*, 5:1221–1227, (1986).

Chanoine et al., *Endrocrinology*, 131:1787–1792, (1992).

Chu et al., *Nucleic Acids Research*, 18:1531–1539, (1990).

Choi et al., Abstract, p. 40, The Fifth Int'l Symp. on Selenium in Biol. & Medicine, Jul. 20–23, 1992 Vanderbilt University School of Medicine, Nashville, TN.

Esworthy et al., *Archives of Biochemistry and Biophysics*, 286:330–336, (1991).

Hatfield, Abstract, p. 4, The Fifth Int'l Symp. in Biol. & Medicine, Jul. 20–23, 1992. Vanderbilt University School of Medicine, Nashville, TN.

Hatfield, *TIBS*, pp. 201–204, (May 1985).

Hawkes et al., *Biochimica et Biophysica Acta*, 699:183–191, (1982).

Herrman, *Biochimica et Biophysica Acta*, 500:61–70, (1977).

Herzog et al., Abstract, p. 44, The Fifth Int'l Symp. in Bio. & Medicine, Jul. 20–23, 1992. Vanderbilt University School of Medicine, Nashville, TN.

Hill et al., *The Journal of Biological Chemistry*, 266:10050–10053, (1991).

Hill et al., *Biochemical and Biophysical Research Communications*, 185:260–263, (1992).

Ho et al., *Nucleic Acids Research*, 16:5207, (1988).

Jaenisch, *Science*, 240:1468–1474, (Jun. 1988).

Knight et al., *J. Nutrition*, 117:732–738, (1987).

Lee et al., *Proc. Natl. Acad. Sci. USA*, 84:6384–6388, (1987).

Lee et al., *The Journal of Biological Chemistry*, 264:9724–9727, (1989).

(List continued on next page.)

*Primary Examiner*—James Ketter
*Assistant Examiner*—Irem Yucel
*Attorney, Agent, or Firm*—Fish & Richardson P.C.

[57] ABSTRACT

Methods of controlling the in vivo and in vitro expression of a heterologous protein by transfecting a cell with a first nucleic acid encoding the heterologous polypeptide, wherein at least one codon of mRNA transcribed from the first nucleic acid is replaced by the codon UGA, and a second nucleic acid operably linked to the first nucleic acid, the second nucleic acid directing the translation of the UGA codon as selenocysteine only when the cell can obtain selenium from the medium in which it is grown; and growing the cell under conditions in which the production of the polypeptide is controlled by the level of selenium available to the cell.

16 Claims, 15 Drawing Sheets

OTHER PUBLICATIONS

Leonard et al., *Biochimica et Biophysica Acta*, 787:122–130, (1984).

Mizutani et al., Abstract, p. 48, The Fifth Int'l Symp. on Selenium in Bio. & Medicine, Jul. 20–23, 1992, Vanderbilt University School of Medicine, Nashville, TN.

Mullenbach et al. *Nucleic Acids Research*, 15:5484, (1987).

Read et al., *The Journal of Biological Chemistry*, 265:17899–17905, (1990).

Speier et al., *The Journal of Biological Chemistry*, 260:8951–8955, (1985).

Sunde et al., Abstract, p. 15, The Fifth Int'l Symp. on Selenium in Bio. & Medicine, Jul. 20–23, 1992, Vanderbilt University School of Medicine, Nashville, TN.

Takahashi, et al., *Blood*, 68:640–645, (1986).

Toyoda et al., *Biochimica et Biophysica Acta*, 1008:301–308, (1989).

Weaver et al., *Genetics*, pp. 451–457, Wm. C. Brown Publishers, Dubuque, Iowa, (1989).

Zinoni et al., *Proc. Natl. Acad. Sci. USA*, 87:4660–4664, (1990).

```
GCGCC                                                                 5

ATG TGT GCT GCT CGG CTA GCG GCG GCG GCG GCC CAG TCG GTG TAT GCC      53
Met Cys Ala Ala Arg Leu Ala Ala Ala Ala Ala Gln Ser Val Tyr Ala
1               5                   10                  15

TTC TCG GCG CGC CCG CTG GCC GGC GGG GAG CCT GTG AGC CTG GGC TCC     101
Phe Ser Ala Arg Pro Leu Ala Gly Gly Glu Pro Val Ser Leu Gly Ser
            20                  25                  30

CTG CGG GGC AAG GTA CTA CTT ATC GAG AAT GTG GCG TCC CTC TGA GGC     149
Leu Arg Gly Lys Val Leu Leu Ile Glu Asn Val Ala Ser Leu SeC Gly
        35                  40                  45

ACC ACG GTC CGG GAC TAC ACC CAG ATG AAC GAG CTG CAG CGG CGC CTC     197
Thr Thr Val Arg Asp Tyr Thr Gln Met Asn Glu Leu Gln Arg Arg Leu
    50                  55                  60

GGA CCC CGG GGC CTG GTG GTG CTC GGC TTC CCG TGC AAC CAG TTT GGG     245
Gly Pro Arg Gly Leu Val Val Leu Gly Phe Pro Cys Asn Gln Phe Gly
65                  70                  75                  80

CAT CAG GAG AAC GCC AAG AAC GAA GAG ATT CAG AAT TCC CTC AAG TAC     293
His Gln Glu Asn Ala Lys Asn Glu Glu Ile Gln Asn Ser Leu Lys Tyr
                85                  90                  95

GTC CGG CCT GGT GGT GGG TTC GAG CCC AAC TTC ATG CTC TTC GAG AAG     341
Val Arg Pro Gly Gly Gly Phe Glu Pro Asn Phe Met Leu Phe Glu Lys
            100                 105                 110

TGC GAG GTG AAC GGT GCG GGG GCG CAC CCT CTC TTC GCC TTC CTG CGG     389
Cys Glu Val Asn Gly Ala Gly Ala His Pro Leu Phe Ala Phe Leu Arg
        115                 120                 125

GAG GCC CTG CCA GCT CCC AGC GAC GAC GCC ACC GCG CTT ATG ACC GAC     437
Glu Ala Leu Pro Ala Pro Ser Asp Asp Ala Thr Ala Leu Met Thr Asp
    130                 135                 140

CCC AAG CTC ATC ACC TGG TCT CCG GTG TGT CGC AAC GAT GTT GCC TGG     485
Pro Lys Leu Ile Thr Trp Ser Pro Val Cys Arg Asn Asp Val Ala Trp
145                 150                 155                 160

AAC TTT GAG AAG TTC CTG GTG GGC CCT GAC GGT GTG CCC CTA CGC AGG     533
Asn Phe Glu Lys Phe Leu Val Gly Pro Asp Gly Val Pro Leu Arg Arg
                165                 170                 175

TAC AGC CGC CGC TTC CAG ACC ATT GAC ATC GAG CCT GAC ATC GAA GCC     581
Tyr Ser Arg Arg Phe Gln Thr Ile Asp Ile Glu Pro Asp Ile Glu Ala
            180                 185                 190

CTG CTG TCT CAA GGG CCC AGC TGT GCC TAG                             611
Leu Leu Ser Gln Gly Pro Ser Cys Ala AM
        195                 200

GGCGCCCCTC CTACCCCGGC TGCTTGGCAG TTGCAGTGCT GCTGTCTCGG GGGGGTTTTC 671

ATCTATGAGG GTGTTTCCTC TAAACCTACG AGGGAGGAAC ACCTGATCTT ACAGAAAATA 731

CCACCTCGAG ATGGGTGCTG GTCCTGTTGA TCCCAGTCTC TGCCAGACCA AGGCGAGTTT 791

CCCCACTAAT AAAGTGCCGG GTGTCAGCAA AAAAAAAAAA A  (SEQ ID NO: 3)    832
```

AUGA→AGGA

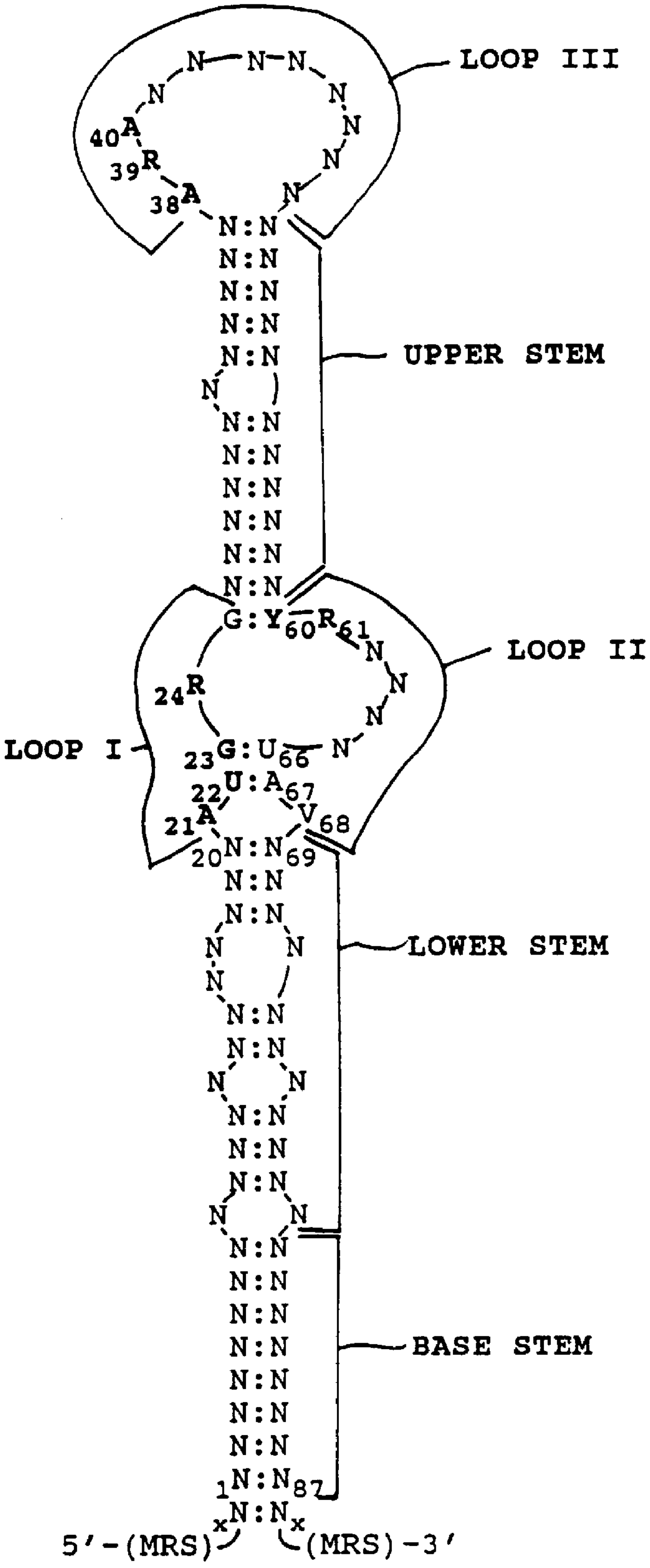
FIG. 9E (SEQ ID NO: 1)

(SEQ ID NO: 2)

POST TRANSCRIPTIONAL GENE REGULATION BY SELENIUM

This application is a continuation-in-part of U.S. Ser. No. 08/066,680, filed May 24, 1993 now abandoned.

STATEMENT OF FEDERALLY SPONSORED RESEARCH

Partial funding of the work described herein was provided by the United States Public Health Service Grants DK41625 and DK38772 and NIH Grants JLL and PEN. The U.S. government has certain rights in this invention.

BACKGROUND OF THE INVENTION

The invention relates to post-transcriptional control of heterologous gene expression by selenium.

One of the major goals of the biotechnology industry is to stably transfect genes encoding proteins of medical and commercial value into cellular and animal systems under conditions that allow control of the expression of the transfected gene. To date, the methods most widely used involve controlling gene expression at the transcriptional level by placing the gene of interest under the control of an inducible promoter. However, the majority of currently available inducible promoters allow the production of significant background levels of gene expression under non-inducing conditions, thus limiting the usefulness of these methods only to applications where low levels of the transfected gene product do not have a significant effect on the cell. Furthermore, most inducible promoters are capable of producing only a limited increase in gene expression (usually about 3-fold) under inducing conditions.

In addition, current methods usually require transfection of the gene of interest into cells which lack the gene product, because the presence of native gene product often results in a signal-to-noise ratio that is difficult to evaluate, and prevents the use of functional assays to examine the transfected gene product. In some instances, when cells lacking the gene product are not available, proteins derived from transfected genes can be differentially identified from native cellular proteins by the addition of small amino acid sequences, termed "epitope tags" or "peptide flags." However, this approach is often limited to applications that do not require functional protein because the added peptide sequence may interfere with a number of processes, including protein folding and post-translational processing, which are essential for the functional activity of the protein.

Selenium can be used by certain organisms to regulate the expression of selenoproteins. Selenoproteins are a unique group of polypeptides that are found in both prokaryotes and eukaryotes and contain the unusual amino acid, selenocysteine. This small group of proteins includes the prokaryotic enzymes in the formate dehydrogenase family, and several eukaryotic polypeptides including the glutathione peroxidase (GPx) enzymes, type I iodothyronine deiodinase, and selenoprotein P. In all of these proteins, selenocysteine incorporation is directed by the universal termination codon, UGA (see, Bock et al., *Trends Biochem. Sci.* 16, 463–467, 1991) and requires both a unique selenocysteine-charged $tRNA^{Ser[Sec]}$ containing the UCA anticodon (Hawkes et al., *Biochim. Biophys. Acta* 699, 183–191, 1982), and specific secondary structural elements in the mRNA (Berry et al., *Nature* 353, 273–276, 1991).

Selenocysteine synthesis is also unique, and the amino acid is formed by the enzyme-catalyzed substitution of selenium for the phosphate of a phosphoserine-charged $tRNA^{[Ser]Sec}$ (see, e.g., Lee et al., *Mol. Cell. Biol.* 10, 1940–1949, 1990). Since selenium is essential to synthesize selenocysteine, removal of selenium from the diet or culture medium leads to a marked reduction in the cellular levels of all selenoproteins (see, e.g., Chanoine et al., *Endocrinology* 131, 479–484, 1992) due to an inability to translate the UGA codon. Thus, the selenium supply determines whether the UGA triplet in a selenoprotein transcript serves as a selenocysteine codon or a stop signal.

Bacteria and mammals differ in the mechanisms by which the translational apparatus interprets a UGA triplet as a selenocysteine codon or as a signal for chain termination. In the MRNA encoding *E. coli* formate dehydrogenase, selenocysteine incorporation at the UGA codon depends on a 40-nucleotide stem-loop located immediately downstream from the UGA and on several critical bases located in the middle of this stem-loop (Zinoni et al., *Proc. Natl. Acad. Sci.* (*USA*) 87, 4660–4664, 1990; Heider et al., *J. Bacteriology* 174, 659–663, 1992). In mammalian mRNA, chain elongation at a UGA codon also depends upon stem-loop structure (s), but they are located in the 3' untranslated region (3'UTR) of selenoprotein transcripts and have been identified as the "selenocysteine-insertion sequence" (SECIS)(Berry et al., 1991) or the "selenium translation element" (STE).

SUMMARY OF THE INVENTION

The invention is based on the discovery that a particular secondary structure and only three short, 2–4 nucleotide segments in the STE are necessary and sufficient for the STE to enable chain elongation at a UGA codon. For example, as described in detail below, in the STE element of the mammalian cellular glutathione peroxidase gene, GPX1, deletions or substitution mutations in any of the three short sequence elements severely diminishes expression of full-length glutathione peroxidase.

Based on this discovery, the invention includes the creation of synthetic or artificial STE elements that can be used to substitute the unique amino acid selenocysteine (SeCys) for one or more amino acids in a polypeptide, e.g., a heterologous polypeptide, to provide a novel method of controlling gene expression at the level of translation.

Accordingly, in one aspect the invention features a method of controlling the production of a heterologous polypeptide in a eukaryotic cell by transfecting a cell with (i) a first nucleic acid encoding the heterologous polypeptide, wherein at least one codon of mRNA transcribed from the first nucleic acid is replaced by the codon UGA, and (ii) a second nucleic acid operably linked to the first nucleic acid, the second nucleic acid directing the translation of the UGA codon as selenocysteine only when the cell can obtain selenium from the medium in which the cell is grown; and growing the cell under conditions wherein the production of the polypeptide is controlled by the level of selenium available to the cell.

The method of the invention can be carried out in vitro in any eukaryotic cell that is capable of being maintained in cell culture. Preferably, the eukaryotic cell is a mammalian tissue culture cell, (e.g., COS-1, HL-60, CV-1, C-6, LLC/PK-1, 3T3L1 or CHO cells) or a yeast cell, e.g., *Saccharomyces cerevisiae.* In one preferred embodiment, the cells used do not contain a native protein which is substantially homologous to the recombinant, heterologous polypeptide. However, in those cases wherein such cells are not available, or have a substantial disadvantage over cells which do contain a homologous native protein, the heterologous polypeptide can be distinguished from the native protein by the increased reactivity of the heterologous polypeptide to nucleophilic reagents due to the presence of the selenocysteine residue, or alternatively, by radiolabeling with the radioisotope $^{75}Se$.

The first and second nucleic acids can be introduced into and maintained in the cell in a recombinant vector that is capable of autonomously replicating in the cell, or stably integrated into the genome of the cell according to standard techniques. The production of the heterologous polypeptide is controlled by the amount of selenium in the medium in which the cells are cultured. When it is desirable to inhibit expression of the polypeptide, the cells are maintained in a medium substantially deficient in available selenium, i.e., the concentration of selenium in the medium is less than 1.0 ng/ml and preferably less than 0.1 ng/ml. To induce expression of the heterologous polypeptide, the cell culture medium typically contains between 1 and 50 ng/ml, preferably 2 to 40 ng/ml, and most preferably 5 to 25 ng/ml.

Alternatively, the method of the invention can be carried out in vivo by stably incorporating the first and second nucleic acids into the genome of an embryonal cell derived from a non-human mammal, and obtaining transgenic progeny of the non-human mammal. "Transgenic" as used herein means a mammal that includes a DNA sequence which is inserted by artifice into a cell, and becomes part of the genome of the animal which develops from that cell. Such a transgene may be partly or entirely heterologous to the transgenic animal. Any non-human mammal that can be produced by transgenic technology is included in the invention; in addition to mice, preferred mammals include rats, cows, pigs, sheep, goats, rabbits, guinea pigs, hamsters, and horses.

As used herein, "embryonal cells" include embryonic stem (ES) cell and fertilized oocytes. In the case of fertilized oocytes, the preferred method of transgene introduction is by microinjection, whereas for ES cells, the preferred method is electroporation. However, other methods including viral delivery systems such as retroviral infection, or liposomal fusion can be used. After introduction of the transgene into an embryonal cell, the cell is introduced into pseudo-pregnant females and progeny is obtained which is heterozygous for the transgene. A stable line of heterozygous animals can then be maintained by appropriate backcrossing to the original animal line, or the heterozygous progeny can be mated to obtain homozygous animals.

When it is desirable to inhibit the expression of the heterologous polypeptide, the transgenic animals are maintained on a diet containing less than 0.02 mg/kg of food, and induction of expression is triggered by supplementing the diet with selenium to a concentration 0.1 mg/kg or higher.

The polypeptide encoded by the first nucleic acid can be any desired polypeptide for which the nucleotide sequence is known. Methods of modifying the polypeptide to incorporate a selenocysteine amino acid residue are described herein. The selenocysteine residue is preferably substituted for a naturally occurring cysteine or an amino acid at a position in the polypeptide that does not abolish the normal biological activity of the naturally occurring protein, e.g., a nonessential amino acid. Such amino acids can be identified by means well known to those skilled in the art, and will usually occur at positions that are not involved in the catalytic or binding activity of the protein (as determined for example by mutational analysis), or at positions considered critical for the structural integrity of the polypeptide (e.g., as predicted by computer analysis or crystallography).

In preferred embodiments, the second nucleic acid includes a contiguous sequence of nucleotides capable of forming a stem-loop secondary structure (also referred to as an STE) in the mRNA transcribed from the second nucleic acid, wherein the stem-loop formed by the mRNA is capable of directing the translation of the UGA codon as selenocysteine. In one preferred embodiment, the second nucleic acid is derived from approximately 90 contiguous nucleotides from the 3' untranslated region of a gene encoding a naturally occurring mammalian selenoprotein. For example, the second nucleic acid comprises a nucleotide sequence substantially homologous or identical to nucleotides 654 to 740 of the human selenoprotein, glutathione peroxidase, shown in FIG. 8 (SEQ ID NO:3).

The invention also features a second nucleic acid that is synthetically derived and includes a continuous stretch of at least 79 nucleotides including three stem elements, each having a 5' half and a 3' half, and three loop elements, each having a 5' end and a 3' end. As shown in FIG. 9E (SEQ ID NO:1), the "5' half" of any stem element is on the left side of the figure, and the "3' half" is on right side of the figure. The first nucleotide of the 5' half is $_1N$, whereas the first nucleotide of the 3' half is $N_{87}$.

In this embodiment, as shown, e.g., in FIG. 9E (SEQ ID NO:1), the stem elements include a) a base stem including at least 16 nucleotides in 8 complementary pairs of nucleotides, b) a lower stem including at least 16 nucleotides in 8 complementary pairs of nucleotides, the first nucleotide of the 5' half of the lower stem being bound to the last nucleotide of the 5' half of the base stem, and the first nucleotide of the 3' half of the lower stem being bound to the last nucleotide of the 3' half of the base stem, and c) an upper stem including at least 22 nucleotides in 11 complementary pairs of nucleotides. Further, the loop elements include d) a first loop consisting of 5'-AUGRG-3' (SEQ ID NO:26), the 5'-A being bound to the last nucleotide of the 5' half of the lower stem and the 3'-G being bound to the first nucleotide of the 5' half of the upper stem, e) a second loop consisting of 5'-YRNNNNUAV-3' (SEQ ID NO:27), the 5'-Y being bound to the first nucleotide of the 3' half of the upper stem and the 3'-V being bound to the last nucleotide of the 3' half of the lower stem, and f) a third, apical loop consisting of 5'-ARANNNNNNNN-3' (SEQ ID NO:28), the 5'-A being bound to the last nucleotide of the 5' half of the upper stem and the 3'-N being bound to the last nucleotide of the 3' half of the upper stem. In this, and other embodiments, A is adenine, G is guanine, N is adenine, guanine, cytosine, or uracil, R is guanine or adenine, U is uracil, V is any nucleotide except thymidine or uracil, and Y is uracil or cytosine.

This second nucleic acid can further include a first mutually exclusive multiple cloning site tail attached to the first nucleotide of the 5' half of the base stem and a second mutually exclusive multiple cloning site tail attached to the first nucleotide of the 3' half of the base stem. The second nucleic acid can also include additional pairs of complementary nucleotides in the base and lower stem elements.

In other embodiments, the second nucleic acid is synthetically derived and includes a continuous stretch of 87 nucleotides, wherein a) nucleotides 1 to 8 are complementary to nucleotides 87 to 80, respectively, and when base-paired together form a base stem consisting of 16 nucleotides in 8 complementary pairs of nucleotides, b) nucleotides 9 to 20 and 69 to 79 when base-paired together form a lower stem consisting of at least 8 complementary pairs of nucleotides, c) nucleotides 21 to 25 are 5'-$A_{21}U_{22}G_{23}R_{24}G_{25}$-3' (SEQ ID NO:26) and form a first loop, d) nucleotides 60 to 68 are 5'-$Y_{60}R_{61}N_{62}N_{63}N_{64}N_{65}U_{66}A_{67}V_{68}$-3' (SEQ ID NO:27)

and form a second loop, e) nucleotides 26 to 37 and nucleotides 49 to 59 when base-paired together form an upper stem of at least 11 complementary pairs of nucleotides, and f) nucleotides 38–48 are non-complementary and are $5'\text{-}A_{38}R_{39}A_{40}N_{41}N_{42}N_{43}N_{44}N_{45}N_{46}N_{47}N_{48}\text{-}3'$ (SEQ ID NO:28) and form a third, apical loop.

The invention also features a method of producing a radiolabeled recombinant polypeptide by producing a first nucleic acid encoding the recombinant polypeptide wherein at least one codon of MRNA transcribed from the first nucleic acid has been replaced by the codon UGA; producing a second nucleic acid of the invention operably linked to the first sequence; introducing the first and second nucleic acids into a cell; and growing the cell in the presence of a radioactive selenium isotope under conditions sufficient to allow incorporation of the isotope into the recombinant polypeptide translated from the first and second nucleic acids.

Also featured is a double-stranded nucleic acid which contains DNA encoding the single-stranded nucleic acid of the invention, a nucleic acid having the sequence of FIG. 9E (SEQ ID NO:1), and a nucleic acid having the sequence of FIG. 9F (SEQ ID NO:2).

By "heterologous" nucleic acid is meant a nucleic acid which is partly or entirely foreign to the cell or animal in which it is introduced, or a nucleic acid which is homologous to an endogenous gene of the cell or animal with the exception that the heterologous protein contains selenocysteine substituted for at least one amino acid.

As used herein, the term "operably linked" means that the contiguous stretch of nucleotides which form the stem-loop secondary structure is in sufficient proximity with the nucleic acid encoding the protein to allow translation of any UGA codon in the protein to be translated as selenocysteine. Preferably, the stem-loop is inserted in the 3' untranslated region of the mRNA molecule encoding the polypeptide; preferably within 2000 nucleotides of the UGA codon, more preferably within 400 to 1500 nucleotides, and most preferably within 500 to 1200 nucleotides.

By "functionally active" is meant possessing any in vivo or in vitro activity which is characteristic of the naturally occurring protein.

"Homologous," as used herein, refers to the sequence similarity between two polypeptide molecules or two nucleic acid molecules. When a position in both of the two compared sequences is occupied by the same nucleotide base or amino acid subunit, then the molecules are homologous at that position. Thus, by "substantially homologous" is meant a nucleotide or amino acid sequence that is largely, i.e. 90 percent, but not wholly homologous.

By "heterologous" nucleic acid is meant a nucleic acid which is partly or entirely foreign to the animal in which it is transfected, or a nucleic acid which is homologous to an endogenous gene of the transgenic animal, but which is inserted into the animal's genome at a location which differs from that of the natural gene.

Unless defined otherwise, all technical terms and scientific terms used herein have the same meaning as commonly understood by one of ordinary skill in the art to which this invention belongs. Although any methods and materials similar or equivalent to those described herein can be used in the practice or testing of the present invention, the preferred methods and materials will now be described. All patents and publications mentioned herein are incorporated by reference. In addition, the materials, methods and examples are illustrative only and not intended to be limiting.

The methods of the present invention provide several advantages over currently used methods of gene expression. First, the substitution of SeCys into a polypeptide sequence is absolutely dependent on the supply of selenium, thus allowing virtually absolute control of the amount of transfected gene product at the level of translation. Second, SeCys has all of the biological properties of the amino acid residue Cys, and thus substitution of SeCys for Cys does not result in a significant alteration in the normal biological activity of the transfected gene product. Third, a transfected gene product which contains SeCys can be readily distinguished from native cellular proteins via its heightened reactivity toward nucleophilic reagents, or by $^{75}Se$ incorporation.

Other features and advantages of the invention will be apparent from the following detailed description, and from the claims.

DETAILED DESCRIPTION

The drawings will first be briefly described.

Drawings

FIG. 1A is a schematic diagram of the human cellular glutathione peroxidase cDNA constructs. The open reading frame (ORF) and 3' untranslated region (UTR) are indicated by a wide bar; plasmid elements and 5'UTR are indicated by flanking lines. Nucleotide numbering starts at the beginning of the open reading frame; the ATG initiation codon is at nt 1–3, the TGA selenocysteine codon is at nt 142–144, and the TAG termination codon is at nt 607–609. Arrows indicate the positions of restriction endonuclease sites. Lines below the diagram represent the positions of the indicated deletions. The hatched bar below the diagram shows the position at which the epitope tagging sequence was inserted, and the region of cDNA replaced.

Figure 2A:
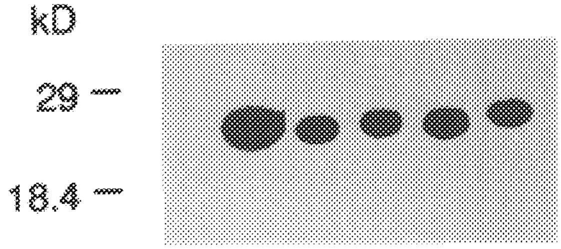

FIG. 2A is an autoradiograph of an SDS-polyacrylamide gel of immunoprecipitated $^{75}Se$-labelled COS-1 cell extracts after transfection with pCMV4 (lane 1), native GPx (lane 2), or deletion mutants ORF-D1 through ORF-D4 (lanes 3–6, respectively).

Figure 2B:
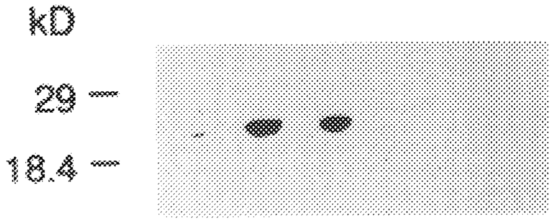

FIG. 2B is an autoradiograph of an SDS-polyacrylamide gel of immunoprecipitated $^{75}Se$-labelled COS-1 cell extracts after transfection with pCMV4 vector (lane 1), native GPx (lane 2), or deletion mutant ORF-D5 (lane 3).

Figure 3:
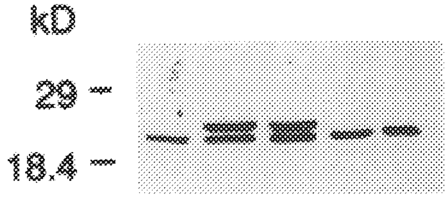

FIG. 3 is an autoradiograph of an SDS-polyacrylamide gel of immunoprecipitated $^{75}Se$-labelled COs-1 cell extracts after transfection with pCMV4 vector (lane 1), epitope-tagged GPx (lane 2), or deletion mutants UTR-D1 through UTR-D3 (lanes 3–5, respectively).

Figure 4:
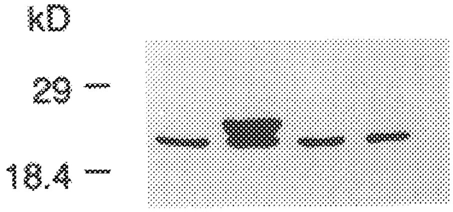

FIG. 4 is an autoradiograph of an SDS-polyacrylamide gel of immunoprecipitated $^{75}Se$-labelled COS-1 cell extracts after transfection with pCMV4 vector (lane 1), epitope-tagged GPx (lane 2), deletion mutant UTR-D4 (lane 3), or deletion mutant UTR-D5 (lane 4).

Figure 5:
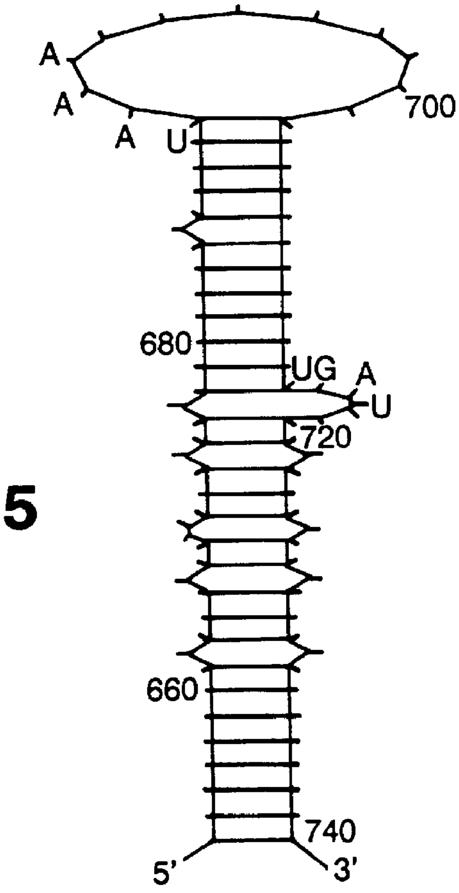

FIG. 5 is a schematic diagram of the potential secondary structure of the 3'UTR of human GPx mRNA.

Figure 6:
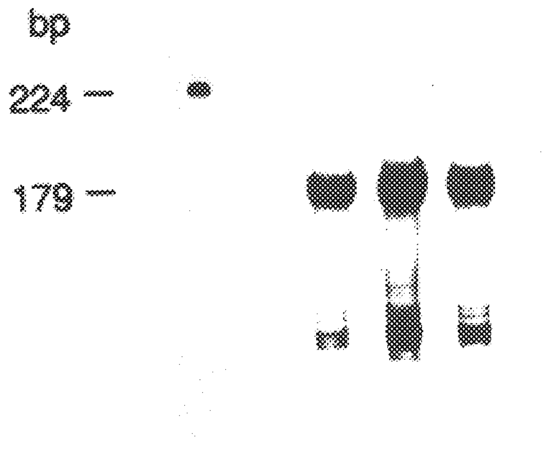

FIG. 6 is an autoradiograph of a polyacrylamide gel of the products of an RNase protection assay using a labeled riboprobe. Lane 1, undigested probe; lane 2, probe hybridized with RNA from untransfected COS-1 cells; lane 3, probe hybridized with epitope-tagged GPx COS-1 transfectants; lane 4, probe hybridized with UTR-D4 COS-1 transfectants; lane 5, probe hybridized with UTR-D5 COS-1 transfectants.

Figure 7:
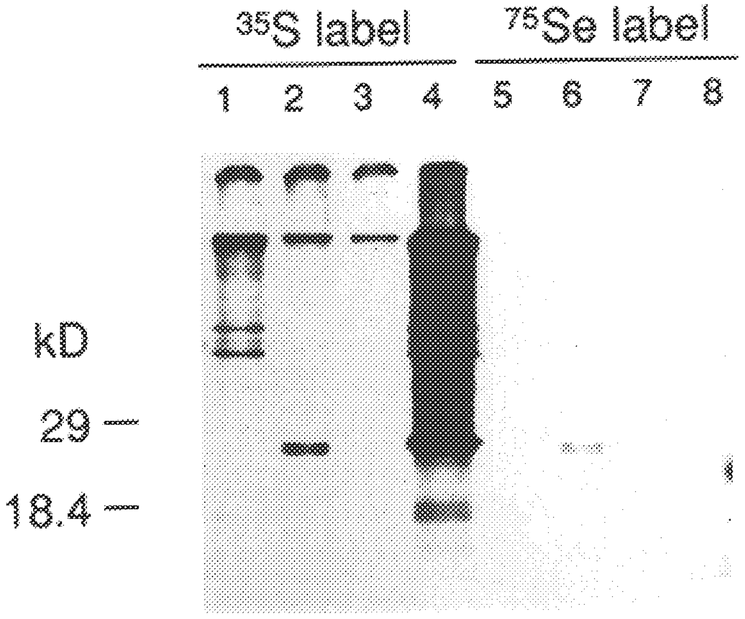

FIG. 7 is an autoradiograph of an SDS-polyacrylamide gel of immunoprecipitated $^{35}$S-labeled (lanes 1–4) and $^{75}$-Se-labeled (lanes 5–8) COS-1 cells transfected with rab5b opal mutants and fusion constructs. Lanes 1 and 5, pCMV4 vector; lanes 2 and 6, rab5b(opal)GPx3'UTR; lanes 3 and 7, rab5b(opal); lanes 4 and 8, rab5b(wt)GPx3'UTR.

FIG. 8 is a schematic depicting the nucleotide sequence of the human glutathione peroxidase gene including the 3'UTR (SEQ ID NO:3).

Figure 9A:
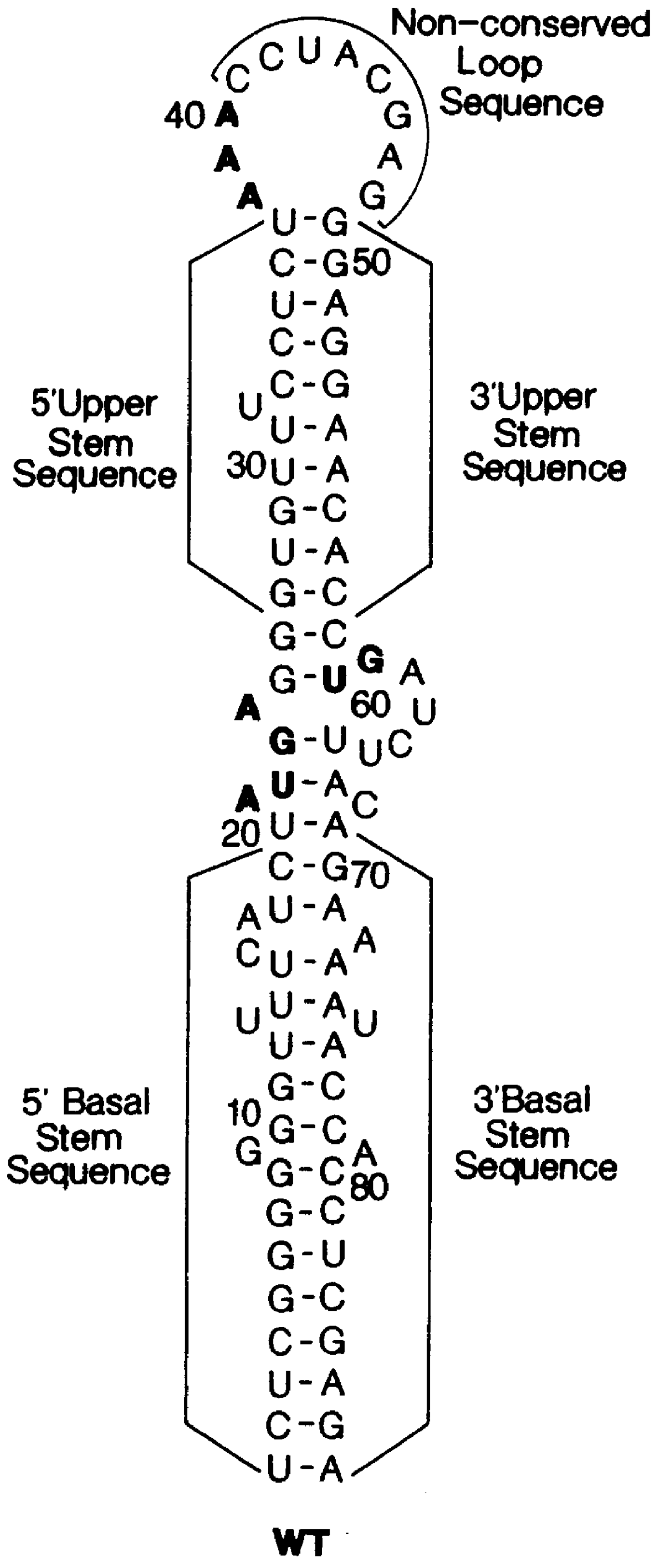

FIGS. 9A to 9D are schematic diagrams of computer (FOLDRNA program) predictions of the sequence and secondary structure of the selenium translation element (STE) of wild-type human glutathione peroxidase (FIG. 9A; SEQ ID NO:33), and various mutated forms, AAA→CAU (9B), UG→GU (9C), and AUGA→AGGA (9D).

FIG. 9E is a schematic diagram depicting an "optimized" STE (SEQ ID NO:1).

Figure 9B:
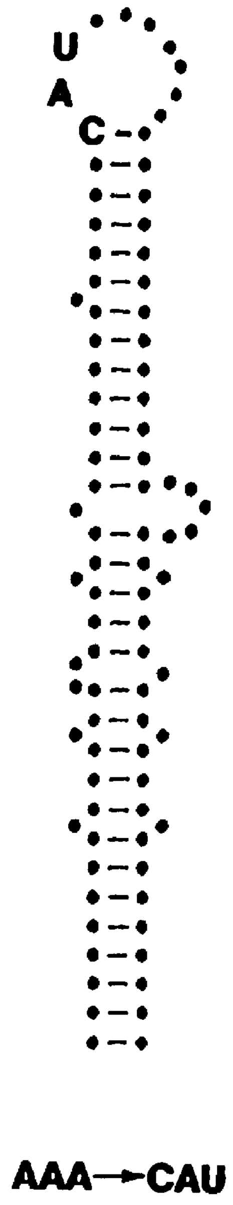
Figure 9C:
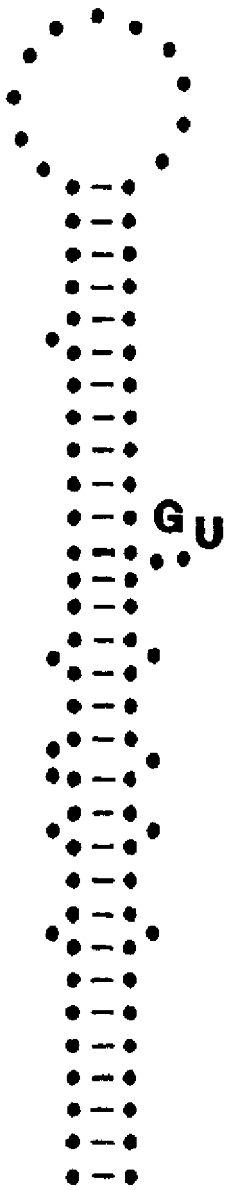
Figure 9D:
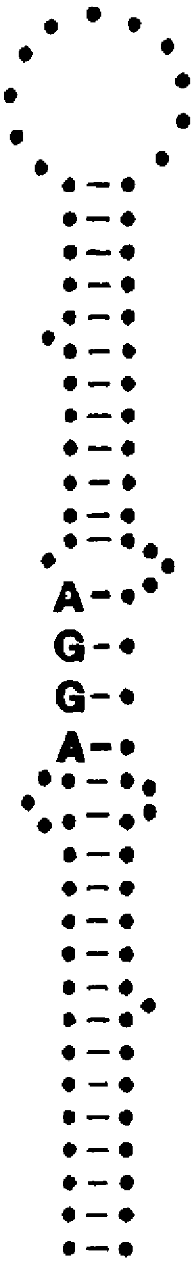
Figure 9F:
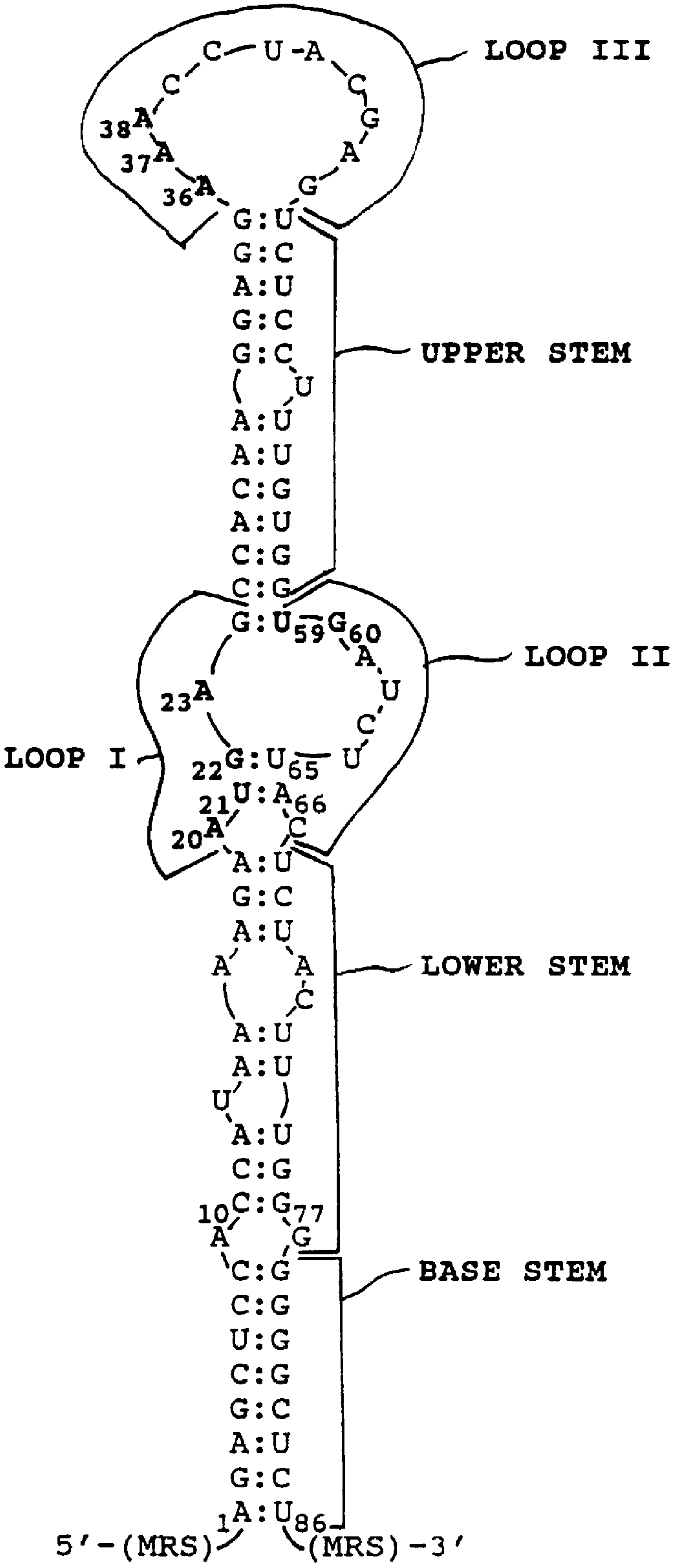

FIG. 9F is a schematic diagram depicting a particular synthetic STE (SEQ ID NO:2).

Figure 10:
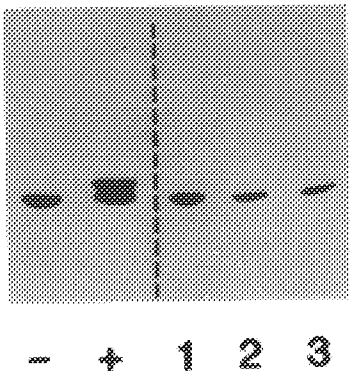

FIG. 10 is an autoradiograph of a representative SDS-PAGE of immunoprecipitated endogenous glutathione peroxidase (lower bands) and transfected, epitope-tagged glutathione peroxidase (upper bands), and shows the effects of deletions of the basal stem, upper stem, and the non-conserved apical loop sequences on the function of GPX1 STE.

Figure 11:
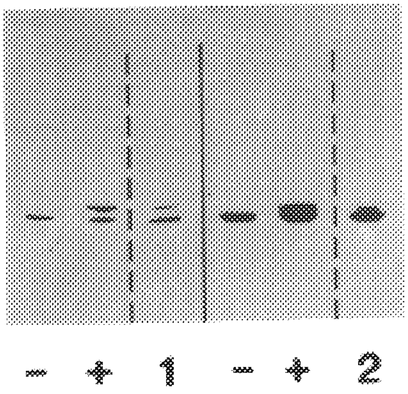

FIG. 11 is an autoradiograph of immunoprecipitated GPx showing the effects of stem exchange and apical loop inversion on the function of the GPX1 STE.

Figure 12A:
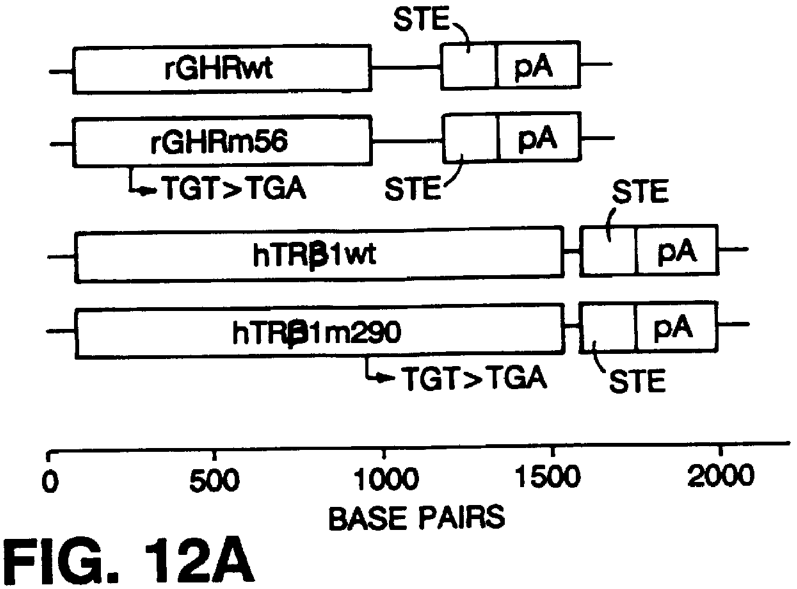

FIG. 12A is a schematic representation of cDNA.STE constructs using rat growth hormone receptor (rGHR) and human thyroid hormone receptor β1 (hTRβ1).

Figure 12B:
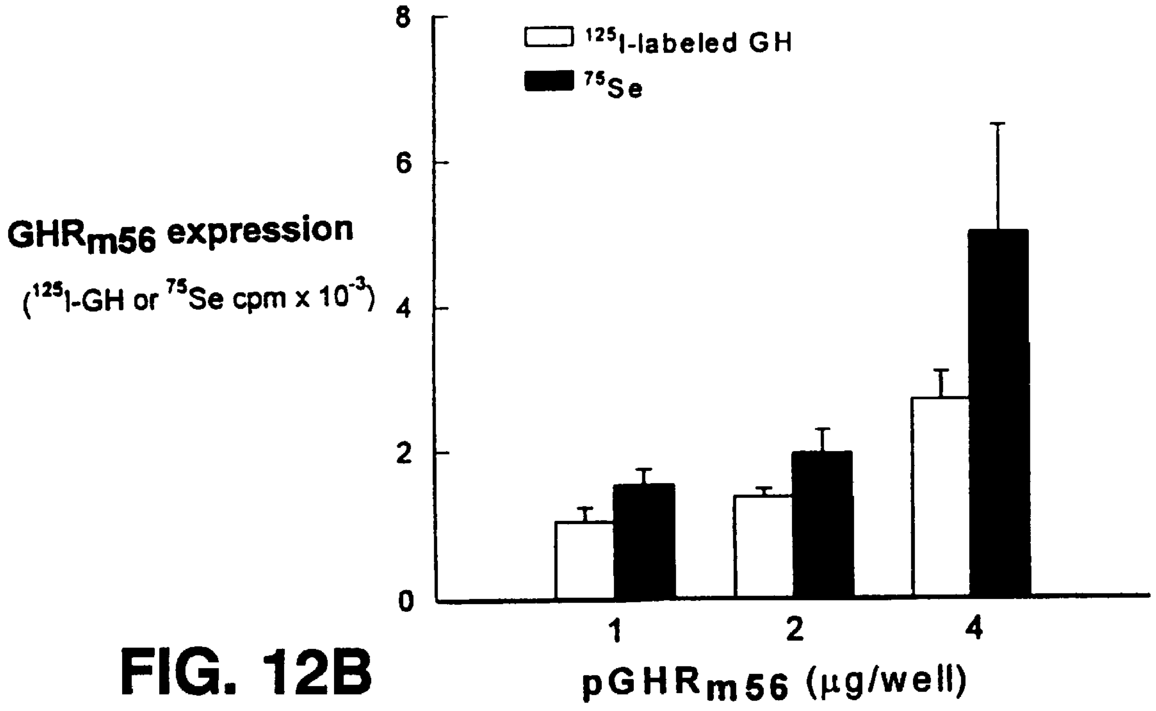

FIG. 12B is a graph showing expression of UGA (opal) mutant GHRs.

Figure 12C:
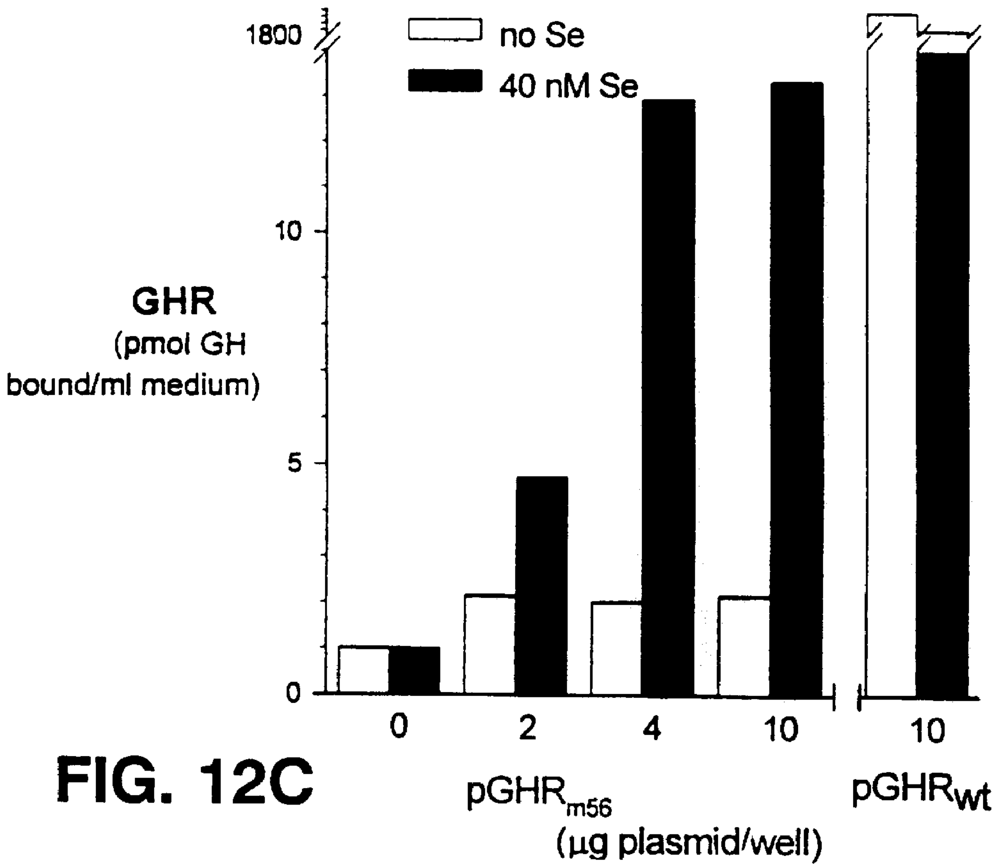

FIG. 12C is a graph showing selenium-dependent expression of opal mutant GHRs.

Figure 12D:
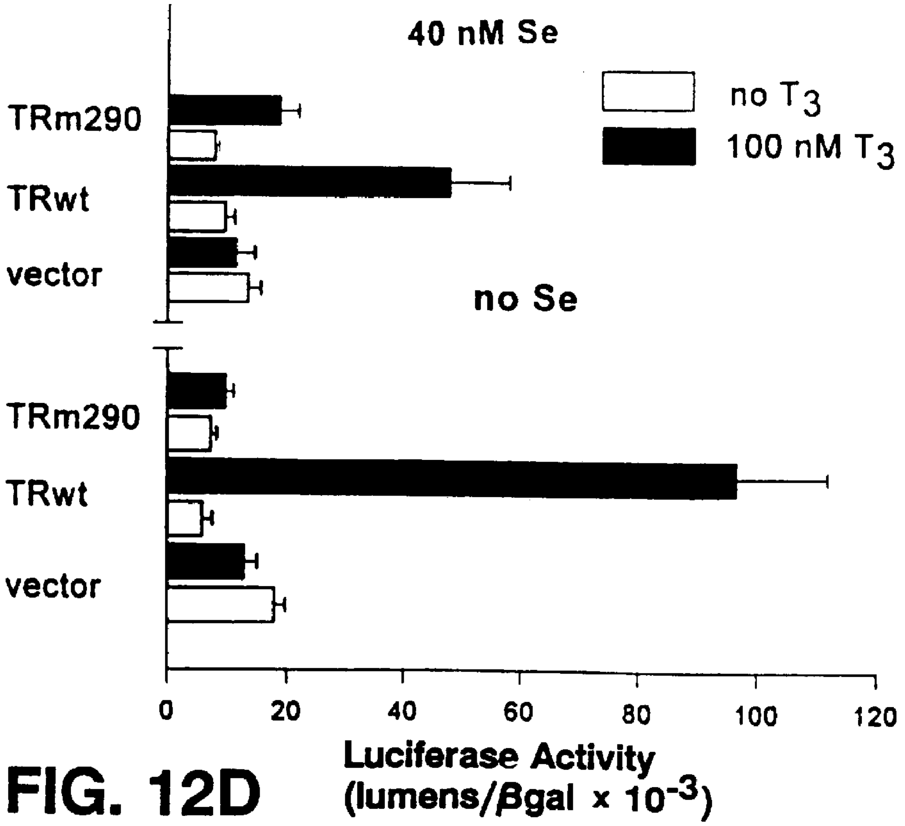

FIG. 12D is a graph showing selenium-dependent expression of functional opal mutant TRβ1.

Figure 13D:
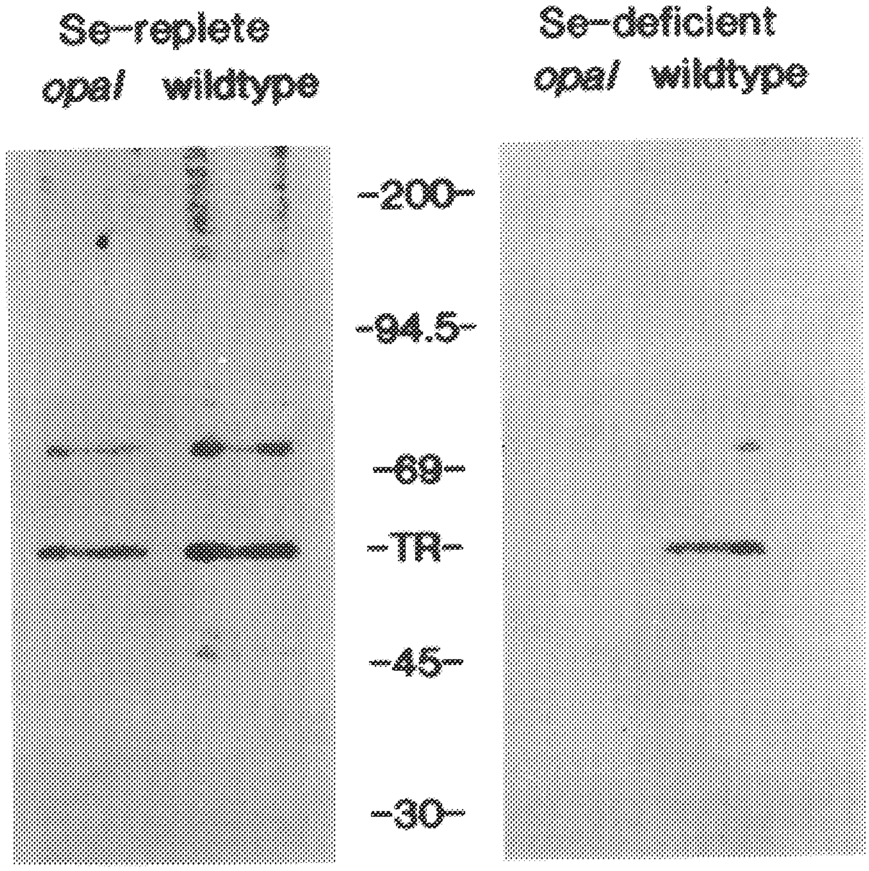
Figure 13A:
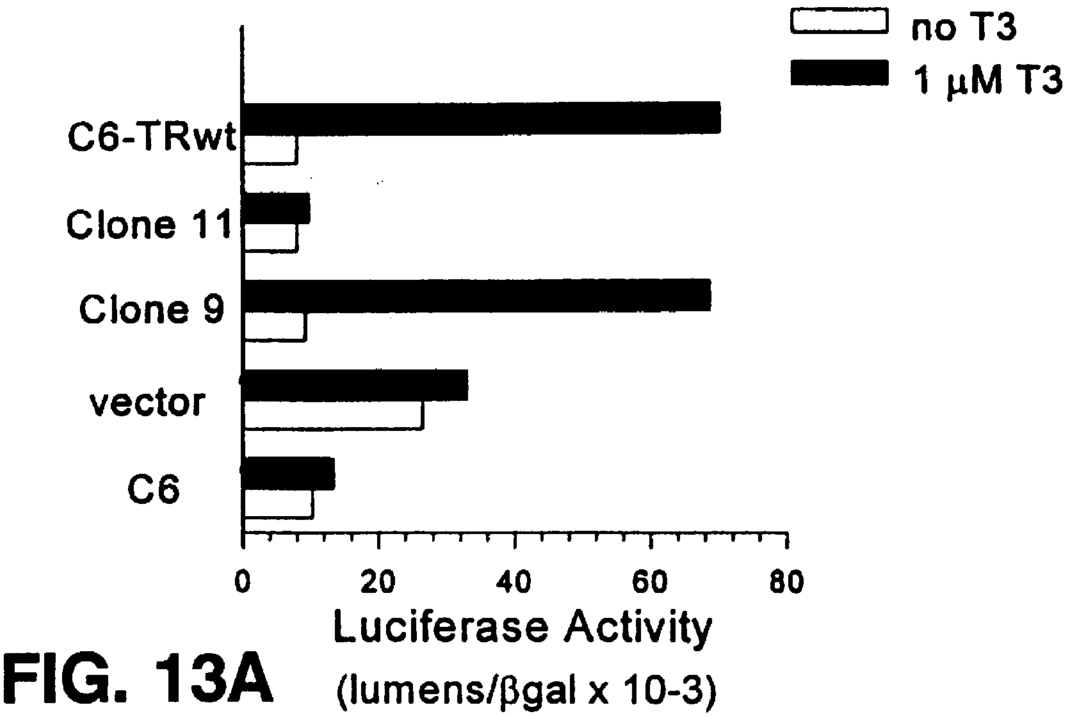

FIG. 13A is a graph identifying C6 cell lines that constitutively express the opal mutant of TRβ1.

Figure 13B:
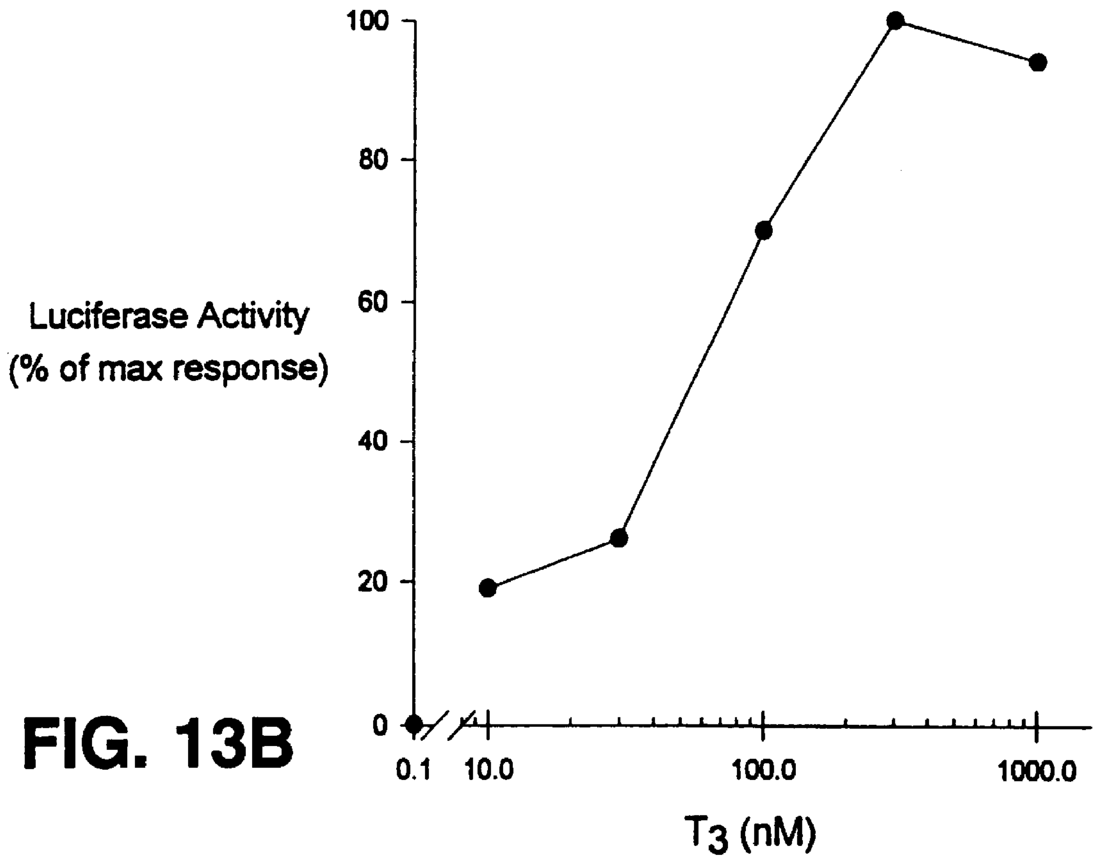

FIG. 13B is a graph showing $T_3$-dependent reporter expression in Clone 9 cells.

Figure 13C:
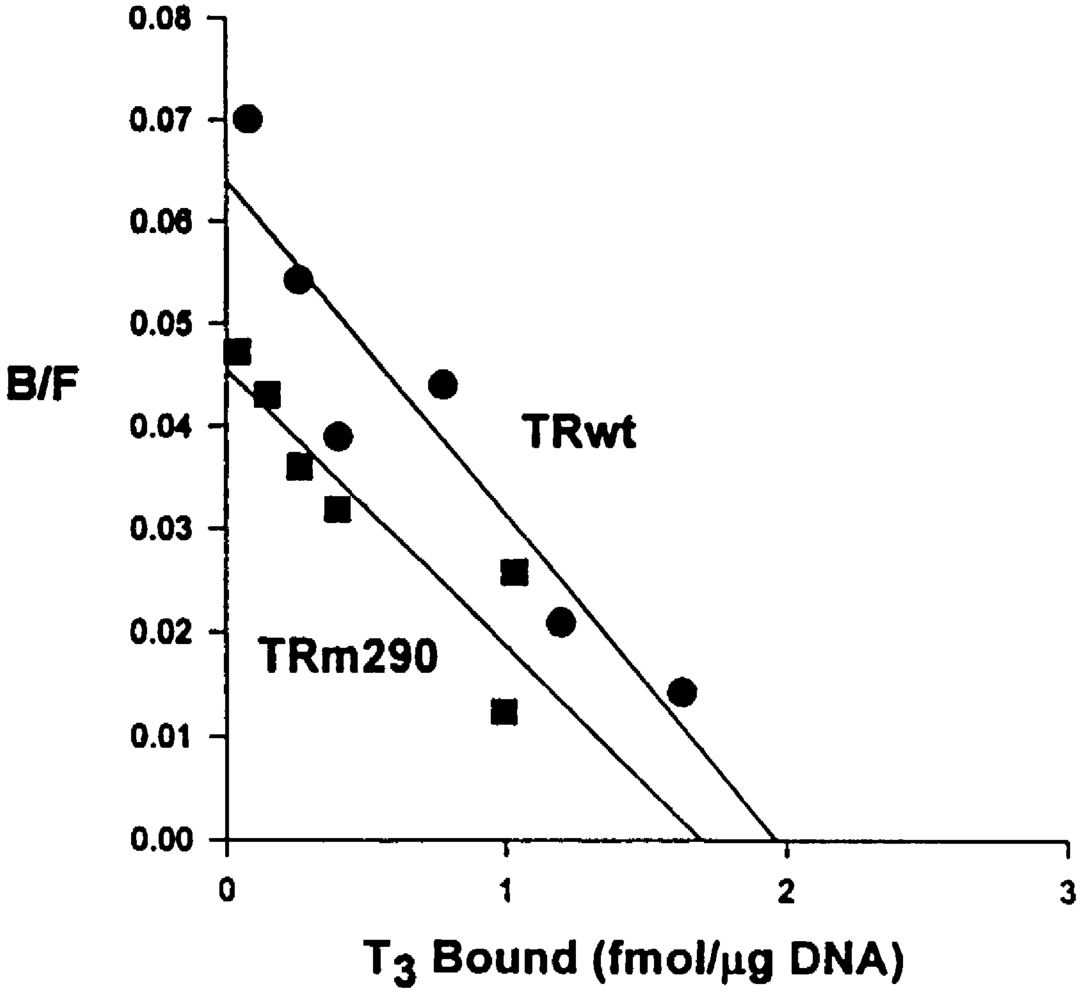

FIG. 13C is a Scatchard plot of nuclear $T_3$-binding in clone 9 and C6TRwt cells.

FIG. 13D is an autoradiograph showing selenium-dependence of nuclear TR localization.

FIGS. 14A to 14F are a series of immunofluorescence micrographs showing how selenium-regulated expression of the opal mutant of TRβ1 determines the hormone-dependent expression of myelin basic protein.

Selenocysteine-Containing Proteins

A small number of eukaryotic and prokaryotic proteins, including bacterial formate dehydrogenases, the mammalian glutathione peroxidase (GPx) family (Mullenbach et al., *Nucleic Acids Res.* 15:5484, 1987; Chambus et al., *EMBO J.* 5:1221, 1986; Esworthy et al., *Arch. Biochem. Biophys.* 286:330, 1991; Takahashi et al., *Blood* 68: 640, 1986), type I iodothyronine 5'deiodinase (Berry et al. (1991) *Nature* 349, 438–440), and selenoprotein P (Read et al. (1990) *J. Biol. Chem.* 265, 17899–17905), belong to a unique group of polypeptides that contains the unusual amino acid selenocysteine.

The production of selenoproteins has been reported to be strictly regulated by the level of exogenous selenium. For example, Knight et al. (*J. Nutr.* 117:732, 1987) reported that glutathione peroxidase activity decreased to undetectable levels in rats given a selenium deficient diet (≦0.02 ppm, 0.016 mg/kg). Chanoine et al. (*Endocrinology* 131:1787, 1992) also reported that rats receiving a selenium deficient diet for six weeks had a significant decrease in both type I and type II 5'-deiodinase levels (≦20% normal). Speier et al. (*J. Biol. Chem.* 260:8951, 1985) demonstrated that, in vitro, glutathione peroxidase activity depended on a selenium concentration in the medium of more than 1 ng/ml, with an optimal activity observed at 5 ng/ml sodium selenate ($2.6\times10^{-8}$M), whereas cells grown in medium without Se supplementation became glutathione peroxidase deficient, with only 1–3% of the activity of Se-supplemented cells. Chada et al. (*Blood* 74:2535, 1989) and Chu et al. (*Nucleic Acids Res.* 18:1531, 1990) also reported a 30 to 50 fold difference in glutathione peroxidase activity between selenium deficient and selenium replete cells.

The control of selenoprotein production by exogenous selenium is believed to occur by post-transcriptional regulation by the incorporation of selenocysteine cotranslationally at a UGA codon (Böck et al. (1991) *Trends Biochem. Sci.* 16, 463–467), which normally acts as a translational stop codon, through the utilization of a unique selenocysteine-charged tRNA containing the appropriate UCA anticodon (Hawkes et al. (1982) *Biochim. Biophys. Acta* 699, 183–191; Lee et al. (1989) *J. Biol. Chem.* 264, 9724–9727). Thus, regulation of selenoproteins most likely proceeds by control of the translation process at the mRNA UGA codon. Selenium incorporated into a selenocysteyl-tRNA would allow translational read through whereas, in the absence of selenium, the selenocysteine tRNA would remain unacylated and the UGA codon would then function to terminate translation.

Since the first identification of the use of the UGA codon for selenocysteine incorporation, a critical question in the interpretation of this "extended genetic code" is how the ribosomal translation assembly can discriminate the special UGA codon in the open reading frame of a selenoprotein mRNA from the termination UGA codon in other mRNA species.

In order to identify all of the elements necessary and sufficient to signal the translation of UGA as selenocysteine, we analyzed the functional importance of sequences from both the open reading frame and the 3' untranslated region (3'UTR) of the gene encoding the human selenoprotein, glutathione peroxidase (GPx), for selenocysteine incorporation in both glutathione peroxidase and in unrelated, heterologous non-selenoproteins.

Construction of GPx and rab5b subclones

GPx subclone GPxR in the vector pBluescript KS (Stratagene) was used as a common template for constructing all GPx deletion subclones. GPXR was derived by inversion of the orientation of a GPX1 cDNA (Chu et al. (1990) *Nucleic Acids Res.* 18, 1531–1539) in the same vector. DNA sequencing of this clone (using standard dideoxy sequencing techniques with a "Sequenase" kit [US Biochemical]) showed one additional GCG codon immediately upstream of the previously reported codon 11 (GCC) (Mullenbach et al. (1987) *Nucleic Acids Res.* 15, 5484; Chada et al. (1990) *Genomics* 6, 268–271), and a codon 92 CTG as we have reported (Chada et al. (1990) *Genomics* 6, 268–271), instead of the CAG observed by Mullenbach et al., *Nucleic Acids Res.* 15, 5484 (1987) (GenBank accession numbers Y00369 and M21304). The former insertion is a polymorphism we have observed in other normal GPX1 sequences.

Unless otherwise indicated, GPx deletion subclones were constructed by overlap extension polymerase chain reaction (PCR) according to standard methods (Ho et al. (1989) *Gene* 77, 51–59), using a Perkin-Elmer Cetus thermal cycler and reagents. This PCR method required two flanking primers defining the size of the final product and two mutually complementary primers directing the desired mutation in the target sequence. The sequences of the flanking primermutagenesine of each pair of complementary mutagenesis primers are listed in Table 1. The final PCR products were inserted back into pBluescript KS, and the sequences were confirmed by standard methods. Then, each mutant GPx sequence was subcloned into the eukaryotic expression vector pCMV4 (Andersson et al., *J. Biol. Chem.* 264, 8222–8229, 1989) for transfection into COS-1 cells as described below.

For construction of subclones with single and double nucleotide substitutions in the small conserved sequences, the mutually complementary oligonucleotide primers directing a particular substitution were synthesized with a mixture of deoxy-A, C, G, and T, at the desired substitution position (s), and mutagenesis performed either by PCR as above or using the Altered Sites II in vitro Mutagenesis System (Promega).

GPxEPI in pBluescript KS, into the expression vector pCMV4 via the ClaI and SmaI polylinker restriction sites.

The overlap extension PCR method was also used to construct mutant and fusion subclones of the rab5b gene, which encodes a member of Ras-related GTPase superfamily (Wilson et al. (1992) *J. Clin. Invest.* 89, 996–1005). The plasmid pMT2, carrying a 1.6 Kb rab5b cDNA clone, was obtained from D. B. Wilson (Harvard Medical School, Boston, Mass.). The construct rab5b(opal)GPx3'UTR contained a fusion product of the rab5b coding region with an opal (UGA) mutation at codon 63, fused with the GPx 3'UTR sequence. The oligonucleotide sequence of the flanking and mutagenesis primers are listed in Table 1. The 3'PCR flanking primer sequence resulted in the removal of the native rab5b TGA termination codon, and substitution of the last 3 codons of the GPx open reading frame, including its TAG stop codon. The resultant rab5b(opal) mutant was inserted into a pBluescript KS construct containing the entire GPx 3'UTR sequence derived from the ClaI-AvrII double digestion of the native GPxR clone in pBluescript KS. The gene fusion product was then subcloned into pCMV4 as described above.

The same strategy was also used to construct rab5b(WT) GPx3'UTR except, in this case, conventional PCR was

TABLE 1

Primers used for overlap extension polymerase chain reactions for construction of GPx and rab5b subclones

| Nucleotide Sequence (5'→3') | Function |
|---|---|
| 1) GGAAACAGCTATGACCAT (SEQ ID NO: 4) | flanking primers for all |
| 2) GTAAAACGACGGCCAGTG (SEQ ID NO: 5) | GPx deletion subclones |
| 3) AATGTGGCGTCCCTCTGAGACTACACCCAGATGAAC (SEQ ID NO: 6) | primers directing |
| 4) TTACACCGCAGGGAGACTCTGATGTGGGTCTACTTG (SEQ ID NO: 7) | deletion in ORF-D1 |
| 5) AACGAGCTGCAGCGGCGCCTGGTGGTGCTCGGCTTC (SEQ ID NO: 8) | primers directing |
| 6) TTGCTCGACGTCGCCGCGGACCACCACGAGCCGAAG (SEQ ID NO: 9) | deletion in ORF-D2 |
| 7) TGAGGCACCACGGTCCGGCGCCTCGGACCCCGG (SEQ ID NO: 10) | primers directing |
| 8) ACTCCGTGGTGCCAGGCCGCGGAGCCTGGGGCC (SEQ ID NO: 11) | deletion in ORF-D3 |
| 9) CTCGGACCCCGGGGCCTGTTCCCGTGCAACCAG (SEQ ID NO: 12) | primers directing |
| 10) GAGCCTGGGGCCCCGGACAAGGGCACGTTGGTC (SEQ ID NO: 13) | deletion in ORF-D4 |
| 11) ATCGAGAATGTGGCGTCCTGAGGCACCACGGTCCGG (SEQ ID NO: 14) | primers directing |
| 12) TAGCTCTTACACCGCAGGACTCCGTGGTGCCAGGCC (SEQ ID NO: 15) | deletion in ORF-D5 |
| 13) ATGAGGGTGTTTCCTCCCTACGAGGGAGGAAC (SEQ ID NO: 16) | primers directing |
| 14) TACTCCCACAAAGGAGGGATGCTCCCTCCTTG (SEQ ID NO: 17) | deletion in UTR-D4 |
| 15) ACGAGGGAGGAACACCCTTACAGAAAATACCA (SEQ ID NO: 18) | primers directing |
| 16) TGCTCCCTCCTTGTGGGAATGTCTTTTATGGT (SEQ ID NO: 19) | deletion in UTR-D5 |
| 17) CGATAGCGCCATGTACCCATACGACGTCCCAGACTACGCTCGG (SEQ ID NO: 20) | primers for epitope sequence tagging |
| 18) CTAGCCGAGCGTAGTCTGGGACGTCGTATGGGTACATGGCGCTAT (SEQ ID NO: 21) | |
| 19) ATATATCGATATGACTAGCAGAAGCACAGC (SEQ ID NO: 22) | flanking primers |
| 20) ATATATCCTAGGCACAGTTGCTACAACACTGGCTCTT (SEQ ID NO: 23) | for rab5b constructs |
| 21) TTCCTCACCCAGTCCGTTTGACTAGATGACACAACAGTG (SEQ ID NO: 24) | primers directing |
| 22) AAGGAGTGGGTCAGGCAAACTGATCTACTGTGTTGTCAC (SEQ ID NO: 25) | an opal mutation in rab5b |

GPx subclones with a partial or complete deletion of the 3'UTR sequence were constructed by conventional DNA recombination techniques. In brief, the subclone UTR-D3, in which the entire GPx 3'UTR was deleted, was constructed by excision of a 250 nt AvrII-SpeI fragment from the epitope-tagged GPx subclone GPxEPI in pBluescript KS, followed by religation of the remaining large fragment. Subclone UTR-D2 was constructed by excision of the AvrII-XhoI fragment followed by religation of the remaining large fragment in the GPx 3'UTR sequence from GPxEPI-containing pBluexcript KS with the plasmid XhoI site eliminated. The subclone UTR-D1 was obtained by inserting a GPxEPI containing fragment with a sticky ClaI end and an end-filled XhoI end, excised from the construct applied using only the flanking primers, and the fusion product (WT, i.e. wild type without the opal mutation) was inserted into pCMV4. The construct rab5b(opal), which contains the coding region opal mutation but the native rab5b 3'UTR, was constructed by fusion of the approximately 900 nt NheI-EcoRI fragment of the rab5b 3'UTR sequence with the rab5b(opal)Gpx3'UTR subclone, from which the GPx 3'UTR had been deleted as an AvrII-EcoRI fragment. The resulting rab5b(opal) sequence was then inserted into pCMV4 as above.

Transfection, Labeling, and Lysis of COS-1 Cells

COS-1 cells were transfected for transient expression of the GPx or rab5b constructs or GPx subclones by modified calcium phosphate mediated or electroporation methods (Maniatis et al. (1990) *Molecular Cloning: A Laboratory Manual* Cold Spring Harbor Laboratory, Cold Spring Harbor), and then cultured in DMEM medium supplemented with 10% fetal bovine serum, 5 ng/ml sodium selenite, 25 mM HEPES pH 7.4, and 1× penicillin-streptomycin-fungizone (Gibco-BRL). All experiments were performed 2–4 times.

As a control for transfection efficiency, COS-1 cells were cotransfected with 2 μg of plasmid pXGH5 included in a human growth hormone transient expression assay system supplied by Nichols Institute. Human growth hormone secreted into the medium was detected by radioimmunoassay using the Crystal Multidetector RIA System (United Technologies Packard).

"Epitope tagging" of GPx was performed (as diagrammed in FIG. 1A) by replacing the first 12 nucleotides (nt) of the open reading frame of GPx with a 30 nt sequence encoding an ATG start codon followed by 27 bases encoding a nine amino acid epitope of human influenza hemagglutinin protein (Chada et al., *Blood* 74, 2535–2541, 1989). The two oligonucleotides listed in Table 1 (SEQ ID NOS:20 and 21) were annealed, then the resulting short double-stranded fragment was inserted into GPx wild-type or mutant subclones in pBluescript KS and/or pCMV4 via the ClaI and NheI restriction sites. In this process, amino acids 2 through 4 of GPx were deleted, producing an epitope-tagged "GPx-EPI" possessing a net increase of six amino acid residues more than wild-type GPx. Although rabbit antiserum against this epitope was available, its binding to tagged GPx molecule was much lower than that of the antisera against GPx peptide sequences, so the latter was still used to detect the tagged GPx molecule.

For $^{75}$Se labeling, 10 μCi of $^{75}$Se as selenous acid diluted in nitric acid, with an original specific activity of 750–1000 Ci/g (from the University of Missouri Research Reactor Facility), was added to the transfected cells in each plate, and the cells were incubated at 37° C. for an additional 2 hours.

For $^{35}$S labeling, the transfected cells in each plate were first incubated for 30 min in methionine- and glutamine-free DMEM medium (Gibco), supplemented with 10% dialyzed calf serum, 1× glutamine (Gibco), and 25 mM HEPES. Then 250 μCi of Express $^{35}$S Protein Labeling mix (NEN DuPont), with a specific activity of 1140 Ci/mmole for methionine, was added to the plate, and the cells were incubated at 37° C. for an additional 2 hours.

After $^{75}$Se or $^{35}$S labeling, 5 or 1 μl (respectively) of diisopropylfluorophosphate was added to ice-cooled labeling mixture in the COS-1 cell plates. After 5 minutes, the mixture was aspirated and 1.5 ml of COS cell lysis buffer (50 mM HEPES pH 7.8, 1% Triton X-100, 10 mM EDTA, 1 mM phenylmethylsulfonyl chloride) was added to each plate. After shaking at 4° C. for 20 minutes, the lysed cell suspension was transferred to a microfuge tube, and subjected to centrifugation at 14,000×g for 10 minutes to remove cell debris. Sodium-dodecyl sulfate (SDS) was added to the supernatant to a final concentration of 0.5%, heated in boiling water for 5 minutes, and then cooled on ice.

Immunoprecipitation and Protein Electrophoresis

Immunoprecipitation utilized two rabbit antisera raised (by Berkeley Antibody Co., Richmond, Calif.) against synthetic peptide sequences from the GPx polypeptide chain, one from residues 26 to 46, and the other from residue 174 to residue 192. Fifteen μl of each antiserum, plus 20 μl of protein A-Sepharose CL-4B beads (Sigma) were added to each lysate, and the mixture was incubated at 4° C. overnight with constant tumbling. The beads were subsequently pelleted, washed twice with washing buffer (50 mM HEPES pH 7.8, 150 mM NaCl, 1% Triton X-100, 0.5% deoxycholate, 0.1% SDS) and once with 50 mM HEPES at pH 7.8, mixed with 30 μl SDS-gel loading buffer (50 mM Tris-HCl pH 6.8, 100 mM dithiothreitol, 2% SDS, 0.1% bromophenol blue, 10% glycerol), heated in boiling water for 3 minutes, and then pelleted in a microfuge. The supernatant was then collected for SDS-polyacrylamide gel electrophoresis (SDS-PAGE).

For COS-1 cells transfected with rab5b constructs, the procedure was the same as above except for the use of 0.2% SDS for cell lysis and the addition of 8μl of affinity-purified rabbit antibody (obtained from D. B. Wilson), raised against a synthetic peptide from the hypervariable domain of rab5b.

Protein electrophoresis was performed by standard techniques (Maniatis et al. (1990) *Molecular Cloning: A Laboratory Manual* Cold Spring Harbor Laboratory, Cold Spring Harbor) on 12% SDS-polyacrylamide gels. Band densitometry of $^{75}$Se-autoradiographs on Amersham-Hyperfilm-Mp was analyzed by ImageMeasure software (Microscience, Inc.).

RNase Protection Assay

Total cell RNA was isolated by the guanidine-HCl method (Ginsburg et al. (1985) *Science* 228, 1401–1406). Riboprobes were generated from the T7 promoter by use of an RNA transcription kit (Stratagene) to synthesize a 224 nt $^{32}$P-labelled RNA transcript complementary to a 179 nt segment starting at the ClaI site of the 5'-untranslated region of the GPxEPI transcript. The template was a ClaI fragment of a construct formed by recircularization of an end-filled SpeI-RsrII large fragment of GPxEPI. RNase protection assays of hybridization mixtures of 3 μg total cell RNA, 10 μg yeast tRNA, and 6 μl of the riboprobe (400,000 TCA-precipitable cpm/μl) were performed by standard techniques (Maniatis et al. (1990) *Molecular Cloning: A Laboratory Manual* Cold Spring Harbor Laboratory, Cold Spring Harbor).

Role of the Open Reading Frame

Figure 1A:
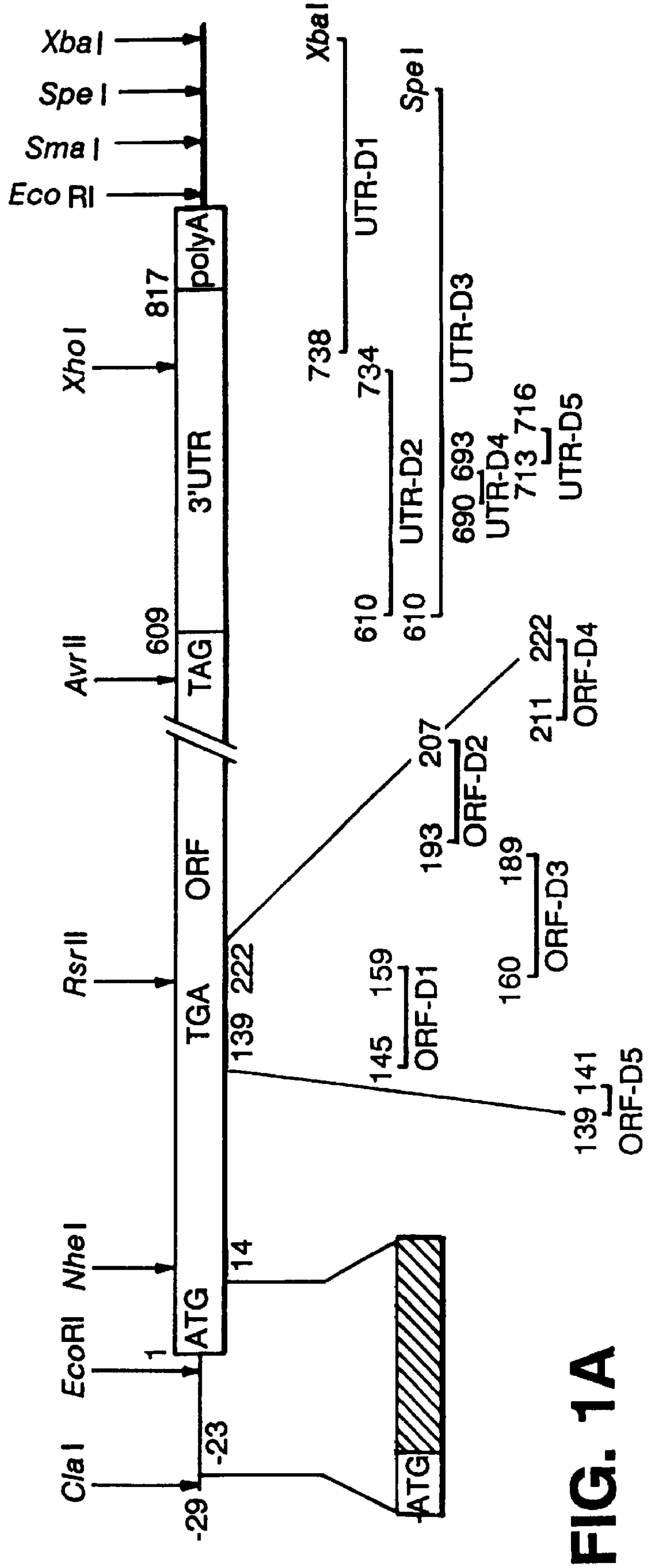
FIG. 1B is a schematic diagram of the potential secondary structure immediately downstream of the $UGA_{142}$ selenocysteine codon in the coding region of the human GPx mRNA, and diagrams the positions of deletions ORF-D1, ORF-D2, ORF-D3, and ORF-D4.
FIG. 1C is a schematic diagram of an alternative potential secondary structure in the coding region of the human GPx mRNA wherein the $UGA_{142}$ selenocysteine codon is within a hairpin structure. The deletion ORF-D5 is also indicated.

We first explored the possibility that nucleotide sequences within the open reading frame (ORF) of the GPx mRNA might serve as a signal for selenocysteine insertion. Sequence analysis of GPx mRNA has revealed no conserved sequences which are common to both prokaryotic and eukaryotic selenoprotein mRNAs, but has predicted two possible loop structures around the $UGA_{142}$ codon. $UGA_{142}$ refers to the codon starting at nucleotide 142 of the cDNA sequence of GPx; all nucleotide numbering for GPx starts at the first base of the open reading frame, as indicated in FIG. 1A.

Figure 1B:
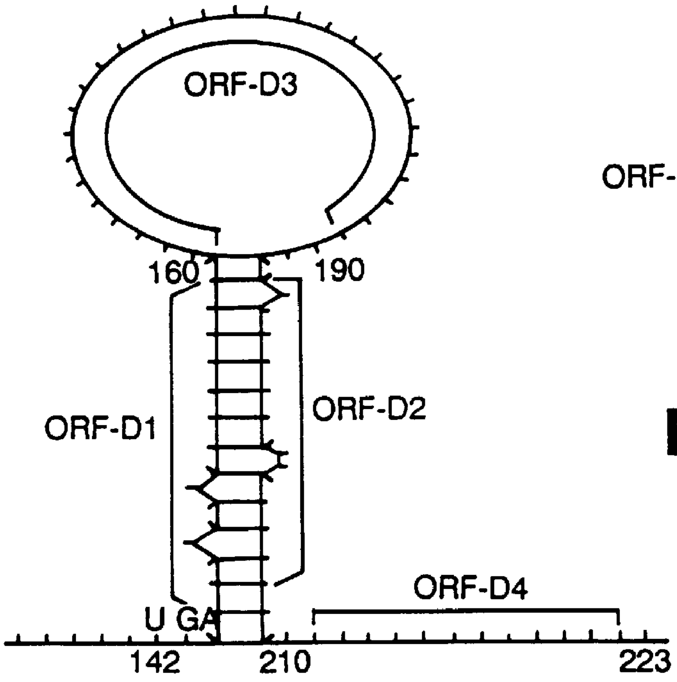
Figure 1C:
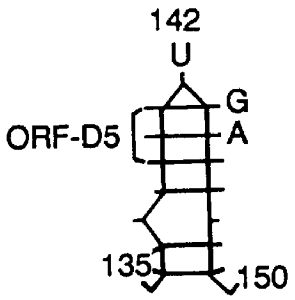

One putative stem-loop structure, immediately downstream of the $UGA_{142}$, creates a stem-loop structure (shown in FIG. 1B) similar to that found in the mRNA of the *E. coli* formate dehydrogenases and related prokaryotic selenoenzyme genes (Zinoni et al. (1990) *Proc. Natl. Acad. Sci. U.S.A.* 87, 4660–4664). Another, which incorporates the $UGA_{142}$ codon at the tip of the "hairpin" (shown in FIG. 1C), is conserved among several mammalian GPx mRNAs, as well as *E. coli* formate dehydrogenase mRNA sequences (Chada et al. (1988) in *Oxy-Radicals in Molecular Biology and Pathology* (Cerutti, P., Fridovich, I., and McCord, J., eds.) pp. 273–288, Alan R. Liss Inc., New York). To test the role of each of these potential secondary structures in the direction of selenocysteine incorporation, we constructed a series of five sequential deletions in the GPx open reading frame, designated ORF-D1 through ORF-D5 which are shown on FIGS. 1A to 1C.

The first four deletion subclones are located within the putative stem-loop region immediately downstream of the $UGA_{142}$ codon. ORF-D1 lacks a sequence from codon 49 through codon 53; ORF-D2 lack codons 65 through 69; ORF-D3 lacks codons 54 through 63; and ORF-D4 lacks codons 71 through 74. The sequences deleted from ORF-D1, ORF-D2, and ORF-D3 correspond, respectively to the 5' part of the stem, the 3' part of the stem, and most (29 of 31 nt) of the loop of the putative stem-loop structure (Zinoni et al. (1990) *Proc. Natl. Acad. Sci.* U.S.A., 87, 4660–4664) in the open reading frame region of GPx mRNA. ORF-D4 represents a 12 nt sequence immediately downstream of the putative stem-loop structure which corresponds to a sequence which has been reported to be important to selenocysteine translation in *E. coli* formate dehydrogenases (Zinoni et al. (1990). GPx subclone ORF-D5 contains a deletion of codon 47, located immediately upstream of the $UGA_{142}$ codon of the GPx mRNA, which forms part of the stem of the alternative, putative hairpin loop structure (Chada et al. (1988) in Oxy-Radicals in *Molecular Biology and Pathology* (Cerutti, P., Fridovich, I., and McCord, J., eds) pp. 273–288, Alan R. Liss Inc., New York). These deletion subclones, carried by the eukaryotic expression vector pCMV4, were individually transfected into COS-1 cells and GPx expression was detected by $^{75}$Se-labeling, immunoprecipitation, SDS-polyacrylamide gel electrophoresis, and autoradiography.

As shown in FIG. 2A, COS-1 cells transfected by the vector alone (lane 1) demonstrate a low background level of $^{75}$Se-containing polypeptide (most likely the native monkey cellular GPx) with a 23 kD size similar to that of human GPx. Transient expression of the native human GPx cDNA and of deletions ORF-D1 through ORF-D4 (lane 2 and lanes 3–6, respectively) all show high levels of $^{75}$Se incorporation into GPx protein. These deletions appeared to exhibit a slight, but not substantial, decrease in GPx expression. Repeated experiments (including the creation of identical deletions in the epitope-tagged construct) also showed slightly diminished expression. Similarly, as shown in FIG. 2B, deletion ORF-D5 produces little or no diminution of selenocysteine insertion into GPx. Thus, while the putative loop structures in the open reading frame of the GPx mRNA may slightly modulate GPx expression, neither is absolutely necessary for translation of the $UGA_{142}$ codon as selenocysteine in human GPx.

Role of the 3'UTR

To test the role of the 3'UTR in selenocysteine insertion, we constructed GPx subclones containing deletions of various lengths in that region as described above. Epitope tags were incorporated into these subclones to improve the resolution of the transiently expressed human GPx products from the COS-1 background. As diagrammed in FIG. 1A, we replaced the first four codons of GPx with a 30 nt sequence encoding an ATG start codon and a 9 amino acid epitope of the human influenza hemagglutinin protein (Chada et al. (1989) *Blood* 74, 2535–2541). The unambiguous discrimination of the transiently expressed, epitope-tagged GPx was possible because the tagged GPx migrated slowly enough on SDS-PAGE gels that its band resolved at a position detectably higher than that of the untagged GPx. This difference of mobility permitted assessment of transient expression of transfected constructs without the need for the substantial overexpression that was necessary to evaluate the coding region deletion constructs described above. The epitope sequence was also inserted into the wild-type GPx subclone GPXR to yield a new GPx subclone GPxEPI, which served as a positive control for the transient expression of the GPx 3'UTR deletion constructs. These deletions are also indicated in FIG. 1A.

The effects of three large deletions of the 3'UTR on [$^{75}$Se]-selenocysteine incorporation into GPx in transfected COS-1 cells are shown in FIG. 3. Lane 1 demonstrates the background GPx signal in cells transfected with vector alone. The slightly larger epitope-tagged GPx is expressed by the GPxEPI construct with its 3'UTR intact (lane 2) and is easily distinguished from the endogenous COS-1 background. Deletion of the distal 100 nt of the 3'UTR (UTR-D1, lane 3) did not diminish expression of the transfected GPx. However, deletion of the proximal 129 nt (construct UTR-D2, lane 4) or the entire 3'UTR (construct UTR-D3, lane 5) completely eliminated detectable $^{75}$Se incorporation into GPx. The distal and entire 3'UTR deletions did not result in a GPx mRNA without a 3'UTR, since the 3'UTR sequence of the human growth hormone gene is built into the pCMV4 vector, so as to fuse to the inserted sequence (if not separated by a transcription termination site, as in the other GPx constructs).

Computer analysis of either the entire GPx mRNA or its 3'UTR sequence using the FOLDRNA program of the University of Wisconsin Computer Group, Inc. (Devereux et al. (1984) *Nucleic Acids Res.* 12, 387–395) revealed a potential secondary structure consisting of a long stem with two small loops (FIG. 5), similar to that found in the 3'UTR of rat and human 5' deiodinase and rat Gpx genes (Berry et al. (1991) *Nature* 353, 273–276). Moreover, two 4-nt sequences within the loop (UAAA in the first and UGAU in the second; indicated in FIG. 5) were identical to those at the same positions within the reported "selenocysteine insertion sequence" motif of the 5' deiodinase gene (Berry et al. (1991) *Nature* 353, 273–276).

To test whether these two short sequences were necessary for selenocysteine insertion into GPx, we constructed two small deletion mutants, UTR-D4 and UTR-D5 (diagrammed in FIG. 1A), that specifically eliminated each of these sequences. The results shown in FIG. 4 demonstrate that either of these short deletions (lanes 3 and 4) completely abolishes detectable selenocysteine incorporation into epitope-tagged GPx in transfected COS-1 cells. Thus, these two short sequences are required for selenocysteine insertion into GPx.

To rule out the possibility that the deletion mutations affect the level of GPx transcripts, we measured levels of GPx mRNA in transfected COS-1 cells by RNase protection assays. As shown in FIG. 6, untransfected COS-1 cells (lane 2, blank) contained no detectable mRNA by a riboprobe specific for the epitope-tagged GPx transcript, and COS-1 cells transfected with epitope-tagged wild-type GPx (lane 3) contain the same amount of transcript as those transfected with the UTR-D4 and UTR-D5 deletions (lanes 4 and 5). Deletions in the open reading frame (ORF-D1, -D2, and -D3) also produced no detectable change in GPx transcript levels (data not shown). Transfection efficiency, assayed by cotransfection with a vector encoding human growth hormone, was also similar from group to group in these experiments (data not shown).

The GPx 3'UTR is Sufficient for Selenocysteine Insertion

Having demonstrated that sequences in the 3'UTR of GPx mRNA are necessary for translational insertion of selenocysteine, we next investigated whether this 3'UTR would be sufficient to direct the same process at a UGA codon in an unrelated coding sequence. The chosen target gene, rab5b, encodes a 25 kD GTP-binding protein which is a member of the Ras-related GTPase superfamily (Wilson et al. (1992) *J. Clin. Invest.* 89, 996–1005). This gene was used for three constructs: rab5b(opal) had codon 63 UGU (cysteine) modified to a UGA (opal) mutant, with the native rab5b 3'UTR; gene fusion construct rab5b(opal)GPx3'UTR consisted of the rab5b(opal) coding sequence fused to a 3' portion of GPx cDNA incorporating the last three codons of the GPx coding region, including its stop codon (UAG), and the entire GPx 3'UTR; and rab5b(wt)GPx3'UTR consisted of the rab5b-GPx fusion product, but carried the wild-type codon 63 rather than the opal mutation. The fusion constructs placed the UGU (cysteine) or UGA (potential selenocysteine) codon the same number of nucleotides upstream from the GPx 3'UTR as in native GPx transcripts.

FIG. 7 presents the results of a representative transient expression experiment of these constructs in COS-1 cells. The expression of rab5b was detected by an affinity-purified rabbit antibody against a synthetic peptide sequence, following either $^{35}$S (lanes 1–4) or $^{75}$Se (lanes 5–8) radioisotope labeling. COS-1 cells transfected with the vector alone (lanes 1 and 5) showed no detectable immunoreactive protein at the appropriate 25 kD molecular mass for rab5b. All three constructs directed the synthesis of a $^{35}$S-labeled polypeptide of approximately 25 kD, at detectable but widely differing levels, but only rab5b(opal)GPx3'UTR, the fusion product of the rab5b with the opal mutation coupled to the GPx 3'UTR, incorporated $^{75}$Se (lane 6). The rab5b (opal) transfectants expressed a very low level of $^{35}$S-labelled protein, probably reflecting the existence of an alternative opal nonsense suppression mechanism (Hatfield, D. (1985) *Trends Biochem. Sci* 10, 201–204) in the COS-1 cells. No $^{75}$Se was detectable even after very long exposures, indicating that no selenocysteine insertion occurred at the UGA codon in the presence of the rab5b 3'UTR. No truncated polypeptide was detectable on $^{35}$S-labelled immunoprecipitates, suggesting that the short polypeptide product was unstable or not immunoreactive with the antiserum. Transfection with the rab5b(wt) GPx3'UTR fusion construct resulted in expression of immunoreactive protein without any detectable $^{75}$Se incorporation, as expected for the wild-type rab5b coding region. For these experiments, transfection efficiency was again confirmed by cotransfection with a vector encoding human growth hormone and measurement of secreted growth hormone.

The importance of the distance between the UGA codon and the selenocysteine-insertion sequence remains unknown. Our target for induced selenocysteine incorporation, rab5b, is similar in amino acid number to GPx, and the codon mutated to UGA is about the same distance (550 nt) from the 3'UTR as the $UGA_{142}$ in GPx. However, in 5'deiodinase the span is approximately 1200 nt, so the precise distance between these elements necessary for selenocysteine incorporation is probably not critical.

These data demonstrate that small segments of the 3'UTR of the human GPx gene, specifically the conserved AAA (loop III) and UGAU (loop II) sequences within the potential stem-loop structure, and not the potential stem-loop or hairpin structures in the coding region, are essential for selenocysteine translation in human GPx. Moreover, these data also demonstrate that the GPx 3'UTR alone is sufficient to signal the translation, as selenocysteine, of an opal mutation (UGA) in the open reading frame of an unrelated non-selenoprotein, rab5b.

Determination of Specific Sequences Required in STEs

To examine the contribution of individual conserved regions of the stem-loop structure to selenocysteine insertion into the mammalian growth hormone peroxidase (GPx) family, we tested three epitope-tagged human GPX1 cDNA constructs with deletions of the basal stem, the upper stem, and the non-conserved apical loop sequence of the wild-type GPx selenium translation element (FIG. 9A; SEQ ID NO:33). Nucleotide numbering in FIG. 9A starts with the "U" at the 5' end of the stem-loop, corresponding to nucleotide 935 of the GPx.

FIG. 10 depicts a $^{75}$Se autoradiograph of a representative SDS-PAGE of immunoprecipitated (from transfected COS-1 cells) endogenous glutathione peroxidase (lower bands) and transfected, epitope-tagged glutathione peroxidase (upper bands). FIG. 10 shows the effects of deletions of the basal stem, upper stem, and the non-conserved apical loop sequences on the function of the GPX1 STE. Lane "–" contains a mock-transfected COS-1, which is a negative control; lane "+" contains a wild-type GPX1 STE, which is a positive control; lane 1 contains a basal stem deletion; lane 2 contains an upper stem deletion; lane 3 contains a non-conserved apical loop deletion.

The first lane (–) shows a single band representing endogenous GPx in COS-1 cells transfected with the vector, pCMV4, alone. The second lane (+) shows the slightly larger, epitope-tagged GPX1 gene product in cells transfected with a construct containing the wild-type GPX1 STE. However, this slower-migrating band was not detectable in lanes 1, 2, or 3, representing cells transfected with the three partial deletion constructs described above. Thus, each major structural feature of the stem-loop, specifically the basal and upper segments of the stem and the non-conserved apical loop, are essential for the function of GPX1 STE (see also Table 2).

We next tested whether STE function could be maintained in constructs that contained major changes in the primary nucleotide sequence of non-conserved portions of the stem-loop, but preserved its overall secondary structure. For that purpose, two epitope-tagged GPX1 cDNA constructs with mutations in its STE were made. In one, the right and left arms of the upper stem were exchanged; in the other, the non-conserved apical loop sequence of the STE was inverted. The FOLDRNA software program (Genetics Computer Group, Inc.) predicted that these mutations would not perturb the overall secondary structure.

As shown in FIG. 11, when the stem exchange construct was expressed in COS-1 cells, epitope-tagged GPX1 expression reached levels comparable with the wild-type control construct (lane 1). Lane "–" contains a mock-transfected COS-1, which is a negative control; and lane "+" contains a wild-type GPX1 STE, which is a positive control. The apical loop inversion construct also directed selenocysteine incorporation into GSH-Px (lane 2), but quantitative measurements of the level of expression indicated that the level of expression was only 56–72% of that provided by the wild-type STE (see also Table 2).

Thus, the overall secondary structure of these segments appears sufficient to permit translation of the coding region UGA as selenocysteine, but some specific sequence or steric information in the non-conserved portion of the apical loop may also be important for STE function.

We further examined the role of specific nucleotide sequences in three very short, 2–4 nucleotide highly-conserved sequences in the GPX1 STE ($A_{21}U_{22}G_{23}A_{24}$, $A_{37}A_{39}A_{40}$, and $U_{60}G_{61}$, see FIG. 9A; SEQ ID NO:33). Single and double nucleotide substitutions were performed in these conserved sequences and examined for their functional effects on the transient expression of epitope-tagged GPX1 in COS-1 cells. In parallel, we used a computer to analyze the possible secondary structure perturbations caused by each substitution. The results are summarized in Table 2 and described below.

TABLE 2

Effects of mutations in the GPX1 STE on selenocysteine incorporation into epitope-tagged glutathione peroxidase

| Mutation | Relative GPX1 Expression (%)[a] | Predicted Perturbation of Secondary Structure[b] |
|---|---|---|
| upper stem deletion[c] | 0,0 | yes |
| basal stem deletion[d] | 0,0 | yes |
| non-conserved loop deletion[e] | 0,0 | yes |
| upper stem exchange[f] | 100,106 | no |
| non-conserved loop inversion[g] | 72,56 | no |
| AAA→GAA | 38,30 | no |
| AAA→ACA | 35,89 | no |
| AAA→AGA | 98,92 | no |
| AAA→AUA | 39,77 | no |
| AAA→GAA | 38,30 | no |
| AAA→AA_ | 72,61 | no |
| AAA→AGG | 57,33 | no |
| AAA→CAU | 0,0 | yes |
| AAA→GAU | 0,0 | no |
| UG→CG | 54,60 | no |
| UG→UA | 40,44 | no |
| UG→AA | 0,0 | yes |
| AUGA→AGGA | 0,0 | yes |
| AUGA→AUCA | 0,0 | yes |
| AUGA→AUGC | 0,0 | yes |
| AUGA→AUGG | 108,112 | no |
| AUGA→AUGU | 77,59 | no |
| AUGA→GGGA | 0,0 | yes |
| AUGA→UCGA | 0,0 | yes |

In Table 2, levels of selenocysteine incorporation were relative to simultaneous control transfection of epitope-tagged GPX1 with the wild-type 3'UTR (note a). The two numbers in the middle column represent the percentages of wild-type expression from two separate experiments. Computer analysis to predict the perturbations of the secondary structure was done using the FOLDRNA program of the Genetics Computer Group, Inc., software package (note b). The upper stem deletion was of nt 26–37 and 49–59 in FIG. 9A (note c). The basal stem deletion was of nt 1–20 and 68–86 in FIG. 9A (SEQ ID NO:33) (note d). The non-conserved loop deletion was of nt 41–48 in FIG. 9A (note e). The upper stem exchange was a complementary exchange of 3' and 5' sides (nt 26–37 and 49–59 respectively) of the upper stem in FIG. 9A (note f). The non-conserved loop inversion was of nt 41–48 in FIG. 9A (note g). Nucleotide numbering in Table 2 (and FIG. 9A) starts with the "U" at the 5' end of the stem-loop, corresponding to nucleotide 935 of the cDNA sequence (Mullenbach et al. 1987). All results represent duplicate independent experiments.

For the non-conserved apical loop region conserved sequence, AAA (FIG. 9A), we obtained four single- and three double-nucleotide substitutions by random oligonucleotide-directed mutagenesis. Expression of epitope-tagged GPX1 expression in COS-1 cells transfected with individual substitution constructs, compared with the wild-type STE, showed that most of the single nucleotide substitutions, as well as a single nucleotide deletion and one double nucleotide substitution, AAA→AGG, resulted in varying degrees of partial loss of selenocysteine incorporation activity. However, the other two double nucleotide substitutions, AAA→CAU (FIG. 9B) and AAA→GAU, caused a total loss of the function. Base pairing of the first C of CAU with nucleotide 49-G adds a base pair in the upper stem and reduces the size of the apical loop. One point mutation, AAA→AGA, preserved normal function, indicating some tolerance for substitution even within this highly conserved sequence.

A similarly wide range of effects was found with nucleotide substitutions in the second conserved sequence UG. The single base mutations UG→CG and UG→UA resulted in a loss of about 50% of selenocysteine insertion function, and the double substitutions of UG→AA and UG→GU (FIG. 9C) resulted in a total loss of GPX1 translation. The latter substitution causes the loss of a base pair between the nucleotide 25-G and the substituted 60-U, plus two new base-pairings: 25-G with 64-C and 24-A with 65-U, with a resultant disruption of the mid-stem "bubbles." Thus, STE function in the GPX1 gene can tolerate most single nucleotide mutations in these two conserved sequences, but is greatly diminished by additional substitutions.

The function of GPX1 STE was more sensitive to nucleotide substitutions in the third conserved sequence, AUGA. The AUGA→AGGA substitution is shown in FIG. 9D.

As shown in Table 2, five single substitutions for each of the first three nucleotides, as well as two double substitutions in this region, all resulted in a total loss of STE function. In the last conserved nucleotide of the short sequence, substitutions of G and U for the wild-type 24-A had no major effect on function; but the substitution of C for the 24-A totally abolished selenocysteine incorporation.

These results confirm the previous deletion experiments in the demonstration of the importance of the three short conserved nucleotide sequences for STE function. However, the substitution mutations also indicate differences in the apparent stringency of the requirements for each sequence element. Reading of the 5' stem conserved sequence AUGA appeared to be the most stringent, with no tolerance for substitutions in the first three bases. The requirement for the apical loop conserved sequence AAA was less stringent, since a single nucleotide deletion and all single and even one double substitution were tolerated to some degree.

To evaluate the effects of the small sequence changes on secondary structure of the STE we examined the predicted structure of the 87-nucleotide STE segment by FOLDRNA program analysis of each mutation (Table 2 and FIGS. 9A to 9D).

For mutations of the AAA sequence segment, computer analysis predicted that only one of the mutations, the double substitution CAU, resulted in a local secondary structure perturbation. As shown in FIG. 9B, this construct allowed formation of an additional base pair on the top of the upper stem, between the first C of CAU and nucleotide 49-G at the 3' end of the non-conserved apical loop sequence (nucleotide numbering in this figure starts with the "U" at the 5' end of the stem-loop, corresponding to nucleotide 935 of the GPX1 cDNA sequence (Mullenbach et al., 1987).

For the conserved UG sequence, the FOLDRNA program predicted that both of the double substitutions that inhibit STE function, but not the innocuous single substitutions, would cause a local perturbation of the secondary structure at the mid-stem bulge. As shown in FIG. 9C, the double substitutions caused a loss of a base pair between the nucleotide 25-G and the substituted 60-U, plus two new base-pairings between 25-G and 64-C and between 24-A and 65-U. Nucleotide 24-A is part of the conserved sequence AUGA that is normally unpaired in the wild-type GPX1 STE.

For mutations within the third conserved sequence, computer analysis further predicted that all the detrimental single- and double substitutions for the first three nucleotide A, U, and G, plus the single substitution of C for the last nucleotide A, resulted in local secondary structure perturbations (Table 2 and FIG. 9D); whereas the innocuous single substitutions of G or U for the last nucleotide A did not alter the local secondary structure.

These results indicate a strong correlation between the functional effects of nucleotide substitutions within the three short conserved sequences of the GPX1 STE and their effects on the secondary structure of the stem-loop. Mutations that perturbed the secondary structure of the stem-loop and its mid-stem bulge profoundly affected STE function, but sequence changes that preserved secondary structure had little or no effect on selenocysteine incorporation. The only exception to the latter rule were mutations in the conserved apical loop sequence, AAA (e.g. AAA→GAA, AAA→GAU).

"Optimized" Synthetic Selenocysteine Insertion Sequences

Examination of the genes encoding various known mammalian selenoproteins indicates that the 3'UTRs have little primary sequence similarity, but have similar potential stem-loop structures (Hill et al., *J. Biol. Chem.* 266:10050, 1991; Zinoni et al. *Proc. Natl. Acad. Sci.* 87:4660, 1990; Ho et al. *Nucleic Acids Res.* 16:5207, 1988; Berry et al., *Nature* 353:273, 1991). This lack of homology between the 3'UTRs of these genes combined with our analyses of the 3'UTR of human glutathione peroxidase, which have demonstrated that three 2 to 4 nucleotide stretches of the putative stem-loop structure are essential for selenocysteine incorporation, have allowed us to design synthetic nucleotide sequences that are capable of forming a stem-loop structure (STE) that contains the essential elements.

This "optimized" synthetic sequence contains a stem-loop containing a "bubble" 16 nucleotides from the base of the stem-loop (the lower stem), followed by an additional 11 nucleotide stem (the upper stem) with an 11 nucleotide apical loop, or balloon, at the top of the structure. The structure of this optimized STE is shown in FIG. 9E (SEQ ID NO:1). In this figure, N is any nucleotide; N:N is any pair of complementary nucleotides; $_xN:N_x$ is any number of pairs of complementary nucleotides; Y is U or C; R is G or A; V is any nucleotide except thymidine (T) or uracil (U); and MRS denotes a multiple restriction site for ease of insertion of the element into any appropriate cloning vector. The key nucleotides are in bold type.

A nucleotide sequence containing the elements of this optimized stem-loop can be constructed by standard techniques known to those skilled in the art of molecular biology. For example, we have synthesized such a synthetic stem-loop, as shown in FIG. 9F, as follows. We synthesized four overlapping oligonucleotides comprising the "loop-bubble-balloon" structure of the STE of GPx using an Applied Biosystems DNA synthesizer and 5'-phosphates were added by polynucleotide kinase. The four oligonucleotides comprising the sense and complementary strands of the stem loop were:

1) Sense Strand (nucleotides 1–50)(SEQ ID NO:29) 5'-CCTAGGAAGAGCTCCACCATAAAAGAATGA-GCCACAAGGAGGAAACCTAC-3'
2) Sense Strand (nucleotides 51–102)(SEQ ID NO:30) 5'-GAGTCTCCTTTGTGGTGATCTTACTCTACTT-TTGGGGGGGCTCTTCTAGAC-3'
3) Complementary Strand (nucleotides 105–61)(SEQ ID NO:31) 5'-TCGAGTCTAGAAGAGCCCCCCC-AAAAGTAGAGTAAGATCACCACA-3'
4) Complementary Strand (nucleotides 60–4)(SEQ ID NO:32) 5'-AAGGAGACTCGTAGGTTT-CCTCCTTGTGGCTCATTCTTTTATGGTG-GAGCTCTTCCTAGG3'

After gel purification, these four single stranded oligonucleotides were annealed and the adjacent ends ligated with T4 DNA ligase. The resultant 105 double-stranded cDNA with AvrII and XbaI 4-base pair overhangs (as shown in FIG. 9F; SEQ ID NO:2) was ligated into the XbaI site of pBluescript, and transformed into XL-1Blue cells. The sequence of the construct was determined by standard dideoxy sequencing strategy.

As shown above, the four-base sequence forming LOOP I (5'-AUGA-3') present on the first part of the apical non-conserved loop tolerates any purine in the second position. Similarly, the base-paired stems can be reversed without consequence. Thus, as shown in FIG. 9E, optimized stem-loop STEs capable of efficient translation of the codon UGA for selenocysteine incorporation can be synthetically produced using the following parameters:

(1) The stem structure of the STE must have a minimum of 8 base-paired nucleotides ("base stem") followed by an additional stretch of base-paired nucleotides ("lower stem") that can tolerate two to four, one to two nucleotide non-complementary base interruptions, such that the base stem is at least 16 base-pairs in length.

(2) LOOP I is comprised of the sequence 5'-AUGRG-3' (SEQ ID NO:26) where R is either an adenine (A) or guanine (G), and the -UG- dinucleotide sequence is capable of pairing with complementary nucleotides contained in LOOP II.

(3) LOOP III (the non-conserved apical loop sequence) is composed of a stretch of 11 non-complementary nucleotides with the sequence 5'-ARANNNNNNNN-3' (SEQ ID NO:28), where R is either an adenine (A) or guanine (G), necessary for stem loop function.

(4) LOOP II is composed of 9 nucleotides with the sequence 5'-YRNNNNUAV-3' (SEQ ID NO:27), where Y is either a cytosine (C) or uracil (U), R is either adenine (A) or guanine (G), and the V is any nucleotide except thymidine (T) or uracil (U). The -UA- dinucleotide is complementary to the -UG- dinucleotide in LOOP I with U pairing with G and the A pairing with U. Guanine has the property of hydrogen bonding with all nucleotides.

By simple examination of other combinations of these base degeneracies, optimized stem loops (STEs) other than the one in FIG. 9F can be synthetically synthesized.

Construction of Recombinant Selenocysteine-containing Polypeptides

We have developed a system for the general application of translational control to heterologous protein expression that exploits the selenium-dependent nature of selenocysteine synthesis and the requirement for a STE to direct selenocysteine incorporation at a UGA codon. Selenium-dependent translation of a target cDNA is achieved by mutating either a codon that encodes a non-essential amino acid or UGU, which encodes cysteine, to a UGA (or TGA), which encodes selenocysteine or termination, and then fusing the mutated coding region to either a synthetic STE, or to the STE from human cellular glutathione peroxidase. The method works for any desired polypeptide for which the DNA sequence is known.

The preparation of these "TGA" ("UGA") mutants is generally accomplished by site-directed or oligonucleotide based mutagenesis techniques, e.g., using commercially available kits (Promega). For example, we have examined the levels of protein expression and the functional consequences of the introduced selenocysteine residue for two selenocysteine mutant proteins of known function, the circulating form of the rat growth hormone receptor (rGHR) and the human thyroid hormone receptor β1 (hTRβ1). As described in further detail below, the cDNA encoding the hTRβ1 was cloned into the multiple cloning site of the vector p-ALTER (Promega) and the cysteine codon at position 290 was mutated to TGA by oligonucleotide based mutagenesis. The cDNA was then rescued by standard laboratory procedure, and the mutation was confirmed by nucleotide sequencing.

Specifically, a 212 nucleotide restriction fragment containing the STE from the 3'UTR of the GPX1 gene provided the downstream stem-loop and sequence elements necessary to interpret UGA as a selenocysteine codon in the constructs shown schematically in FIG. 12A. A synthetic STE as described above and shown in FIGS. 9E and 9F can also be used. The AvrII-XbaI restriction fragment of the GPx1 gene (nt920–1132) containing the 3'UTR STE was ligated into the XbaI site of the expression vector pRC/CMV (Invitrogen) to generate pRC/CMV.STE. Orientation was confirmed by DNA sequencing.

The 1.2 kb rat adipocyte GHRs cDNA (Frick et al., *Endocrinology,* 131:3083–90, 1989) and the 1.7 kb human TRβ1 cDNA (Evans, *Science,* 240:889–95, 1988) were subcloned into the EcoR1 site of pALTER-1 and oligonucleotide-directed mutagenesis performed according to manufacturer's instructions (Promega). A coding region UGA (opal) mutant was generated by mutating the UGU (cysteine) codon to UGA at amino acid position 56 of rGHR (upper pair of constructs in the figure) and at amino acid position 290 of hTRβ1 (lower pair of constructs). The UGA (opal) mutants were confirmed by sequencing with the fmol DNA sequencing kit (Promega).

Constructs were completed by ligation of either opal or wild-type cDNAs into the BstXI site of pRC/CMV-STE. The opal mutant and wild-type cDNAs were inserted 5' to the STE sequence of the GPX1 gene and transcription was terminated by the bovine growth hormone polyadenylation signal in the eukaryotic expression vector pRC/CMV (Invitrogen). The integrity and orientation of each construct was confirmed by DNA sequencing.

In transient expression assays done in COS7 cells, transfection of the opal mutant fusion construct rGHRm56.STE programmed the synthesis and secretion of a full-length, immunoprecipitable growth hormone receptor (FIG. 12B). COS7 cells (75,000 cells/well) were seeded into six well clusters plates (Costar) and transfected in triplicate with increasing amounts of pGHRm56.STE by the $CaPO_4$ coprecipitation as described in Chen et al., *Mol. Cell Biol.,* 7:2745–52 (1987). After 4 hours, the transfection medium was replaced with DMEM/F12 medium supplemented with insulin (20 μg/ml), transferrin (10 μg/ml), hydrocortisone (10 nM), bovine serum albumin (1 mg/ml), penicillin (50 U/ml), and streptomycin (90 μg/ml), and 40 nM $^{75}$Se as Na selenite (150 Ci/g). Cells were grown for 48 hours at 37° C. in a humidified atmosphere containing 5% $CO_2$. GHRs expression was determined in triplicate in 300 μl aliquots of medium by the method of Frick and Goodman, *Endocrinology,* 131:3083–90 (1989), and $^{75}$Se incorporation into the GHRs immuno-precipitate was determined by γ-counting. Data are reported in FIG. 12B as mean ±S.E (n=4).

FIG. 12C shows selenium-dependent expression of opal mutant GHRs. Triplicate wells of COS7 cells were transfected as above with either pGHRm56.STE or pGHRwt.STE, grown for 48 hours in DMEM/F12 with or without 40 nM selenium, and GHRs determined as above. Data are reported as the mean of quadruplicate wells. Co-precipitation of $^{125}$I-labeled growth hormone (open bars) demonstrates that the opal mutant rGHRm56.STE construct retains ligand binding activity, and $^{75}$Se-labeling (hatched bars) of the immunoprecipitated rGHR indicates the incorporation of a selenoamino acid. Scatchard analysis (not shown) revealed that the opal mutation of rGHR did not affect ligand affinity; however, the number of opal rGHR molecules secreted into the culture medium was only 1–3% of that secreted by cells expressing the wild-type rGHR.STE construct. This finding was confirmed by the 30–100 fold greater expression of the wild-type receptor in transfected COS7 cells (FIG. 12C). While the STE is essential for expression of the opal mutant of the rGHR, the presence of the STE in the 3'UTR of the wild-type rGHR construct had little or no effect on the absolute expression levels of the wild-type receptor (data not shown).

As shown in FIG. 12C, expression of the opal mutant rGHRm56.STE construct was entirely dependent upon the presence of selenium in the culture medium. Since the anti-receptor antibody is directed against the C-terminus of the receptor, translation products truncated at amino acid 56 due, to the absence of selenium, are not detected in this functional assay. In contrast, selenium had no effect on expression of the wild-type rGHR.STE construct.

We then examined the opal mutant of the human thyroid hormone receptor (hTRβ1) using a functional reporter assay that requires both ligand binding and signal transduction and transient expression of the hTRβ1.STE constructs. This heterologous reporter system uses a $T_3$-responsive reporter plasmid (pF2H-luc) as described in Spanjaard et al., *Mol. Endocrinology,* 8:286–95 (1993), consisting of a thyroid hormone response element (TRE) from the chick lysozyme gene ($TRE_{F2H}$), the inducible thymidine kinase (TK) promoter, and the luciferase reporter. The results obtained when pF2H-luc was co-transfected into COS7 cells along with the different thyroid hormone receptor constructs are shown in FIG. 12D. COS7 cells (50,000 cells/well) were seeded into 24 well cluster plates (Costar) and transfected by $CaPO_4$ coprecipitation with 0.5 μg pF2H-luc, 0.2 μg pRSVβgal (Promega), and 1 μg of either pRC/CMV.STE (vector), pTRwt.STE, or pTRm290.STE. After a 24 hour recovery period, medium was changed to DMEM/F12 medium ±40 nM selenium and ±100 nM $T_3$ (triiodothyronine) and cells were grown for an additional 72 hours. Luciferase and β galactosidase activities were determined using commercial kits according to manufacturer's instructions. Data are reported as the mean ±SE of quadruplicate wells.

Transient expression of the opal mutant of the thyroid hormone receptor, hTRm290.STE, produced a thyroid hormone receptor capable of mediating the triiodothyronine ($T_3$)-dependent increase in luciferase expression. Like the opal mutants of rGHR, the level of opal TR expression was below that of the wild-type transfectants, presumably due to lower receptor numbers.

The selenium-deficient state eliminates functional expression of the opal TR mutant, but has no effect on expression of the wild-type construct. Without selenium, both the opal mutant hTRm290.STE and wild-type TR.STE control repressed luciferase expression in the absence of $T_3$ when compared to the empty vector controls, due to the well-described dominant negative effect of an unliganded thyroid hormone receptor (Evans, 1988). Since polypeptide chain termination at amino acid 290 in the opal mutant of TR yields a polypeptide containing the DNA-binding domain of the receptor and lacking only the ligand binding domain, the truncated protein should be capable of binding to the TRE of $T_3$-responsive genes.

Thus, the opal mutant-STE fusion constructs of rGHR and hTR direct the selenium-dependent incorporation of selenocysteine at UGA codons, leading to the production of selenium-containing, functional receptor molecules. However, in the transient transfection experiments, the levels of heterologous protein expression fell well below the wild-type controls. This failure to synthesize similar amounts of polypeptide probably reflects the limiting supply of selenocysteine-charged $tRNA^{[Ser]Sec}$, relative to the demands of multiple plasmid copy number and the strong promoters used to over-express the introduced gene products. Alternatively, inefficient interpretation of the opal codon for selenocysteine incorporation may result from losses of a large fraction of the opal mutant mRNA by cytoplasmic editing enzymes that degrade RNAs containing nonsense codons.

Thus, stable transfections were used to evaluate the function of the TR opal mutant. FIG. 13A shows the expression of a functional thyroid receptor in selected clonal lines of rat C6 astrocytoma cells transfected with the opal mutant TRm290.STE construct. C6 astrocytoma cells (100,000 cells) were transfected by $CaPO_4$ coprecipitation with 10 $\mu$g of either pRC/CMV.STE (vector), pRC/CMV-TRwt.STE (TRwt), or pRC/CMV-TRm290.STE (TRopal). After a 24 hour recovery, medium was changed to growth medium (DMEM supplemented with 10% bovine serum, 15 mM HEPES buffer (pH 7.1), penicillin (50 U/ml and streptomycin (90 $\mu$g/ml) and antibiotics), and 200 $\mu$g/ml G418 (Gibco). After 14 days, individual colonies of G418 (neomycin)-resistant cells were isolated by limiting dilution in 96 well microtiter dishes in the presence of G418 (200 $\mu$g/ml). Fifteen G418-resistant cell lines were obtained for TRopal and 24-G418-resistant cell lines for TRwt. Vector cells were a pool of G418-resistant cells without clonal isolation.

TR expression was confirmed by transient transfection with the pF2H-luc reporter plasmid, and analysis of $T_3$-dependent reporter activity. Selected cell lines were seeded (50,000 cells) in quadruplicate into 24 well cluster plates and transfected with 0.2 $\mu$g of pF2H-luc and 0.2 $\mu$g pRSVβgal by $CaPO_4$ coprecipitation and grown for 72 hours in serum-free DMEM/F12±100 nM $T_3$. Luciferase and β-galactosidase activities were determined as described above.

As in the transient expression experiments, cells harboring the opal mutant TRm290.STE construct (clone 9) showed $T_3$-dependent luciferase expression and suppressed reporter expression in the absence of the $T_3$. Several neomycin-resistant C6 clones failed to express the opal TR mutant (e.g., FIG. 13A, Clone 11), presumably due to incomplete integration of a full length TR cDNA into the genome. The $T_3$-dependent C6 cell line, Clone 9, was used in all subsequent experiments.

Clone 9 cells showed a normal dose-response relationship for $T_3$-dependent transactivation of reporter gene expression (FIG. 13B) suggesting adequate receptor affinity and number for the opal TR. Clone 9 cells (75,000 cells/well) were transfected by $CaPO_4$ co-precipitation with 0.2 $\mu$g pF2H-luc and 0.2 $\mu$g of pRSVβgal and cells grown in serum-free DMEM/F12 supplemented with increasing concentration of $T_3$ in triplicate. Reporter activities were determined as described above.

Scatchard analysis (FIG. 13C) of $T_3$ binding to isolated nuclei showed no significant difference between the ligand affinity or receptor number for the TRs derived from TRwt-.STE or the opal mutant TRm290.STE constructs (Table 3). The selenium-dependent expression of the opal mutant TR protein in the clone 9 cells was confirmed by direct immunoprecipitation and by $^{75}$Se-labeling of nuclear proteins. Clone 9 cells and C6TRwt were grown in four 80 $cm^2$ flasks to confluence, cell nuclei prepared as described in Ichikawa et al., *Mol. Cell Endocrinology,* 51:135–42 (1987), and TR determined by T3-binding analysis. Each point of the Scatchard plot was determined in triplicate.

Table 3 presents an analysis of the quantity of nuclear TR in C6.TRwt and clone 9 cells. In Table 3, $T_3$ binding capacity was determined by Scatchard analysis. $^{75}$Se-labeled TR in Clone 9 cells was determined in 0.3M KCl extracts of isolated nuclei. Data are presented as the mean ±SE; the number in parentheses are the number of independent determinations.

TABLE 3

| cell line | integrated CDNA | T3 binding capacity (fmol/$10^6$ cells) | $^{75}$Se-labeled TR (fmol/$10^6$ cells) |
|---|---|---|---|
| C6•TRwt | hTRβ1•STE | 9.5 ± 3.4 (4) | ND |
| clone 9 | hTRm290•STE | 8.0 ± 2.0 (3) | 7.5 ± 1.2 (3) |

SDS-PAGE analysis of anti-TRβ1 IgG immunoprecipitated (FIG. 13D) shows that the opal mutant TRm290 and TRwt fusion constructs produce approximately equal amounts of receptor protein in selenium-replete medium; no immunoreactive TR was found for clone 9 cells grown in the absence of selenium. Clone 9 and C6TRwt cells were grown in triplicate in 25 $cm^2$ flasks to ~80% confluence. Culture medium was changed to serum-free DMEM/F12±40 nM Se for 2 days. In selected flasks 40 nM $^{75}$Se (150 Ci/g) was added. Six hours before harvest, the medium was changed to serum-free DMEM/F12 containing 10 $\mu$Ci/ml $^{35}$S-MET and the cells were labeled for 6 hours. Cell nuclei were prepared as before, TR extracted with 0.3M KCl, and immunoprecipitated with anti-TRβIgG. Immunoprecipitates were resolved by SDS-PAGE under reducing conditions and radioautography performed.

Expression of the chromatin-associated, $^{75}$Se-labeled TR present in the clone 9 cell nucleus was in close agreement with the estimates made by ligand binding Scatchard analysis (Table 3).

Finally, we examined the ability of the opal mutant TRm290.STE to transactivate a native gene using the expression of the $T_3$-dependent, glial cell gene, myelin basic protein. As shown in FIGS. 14A to 14F, myelin basic protein expression showed normal $T_3$-dependence in clone 9 cells in the presence of selenium. Clone 9 and C6TRwt cells were grown on coverslips in serum-free DMEM/F12 medium supplemented ±40 nM Se and/or ±100 nM $T_3$ for 2 days. Cell monolayers were fixed with 4% paraformaldehyde and permeabilized with iced methanol. Myelin basic protein was visualized by indirect immunofluorescence using anti-myelin basic protein IgG from Boehringer-Mannheim, and Texas Red conjugated Goat anti-Rabbit IgG from Amersham.

Figure 14A:
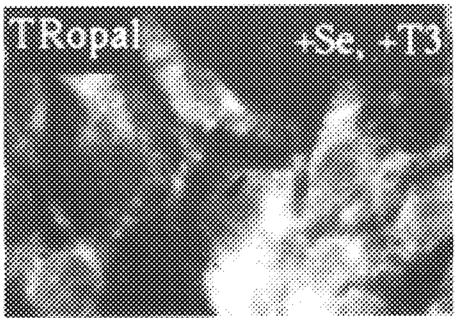
Figure 14B:
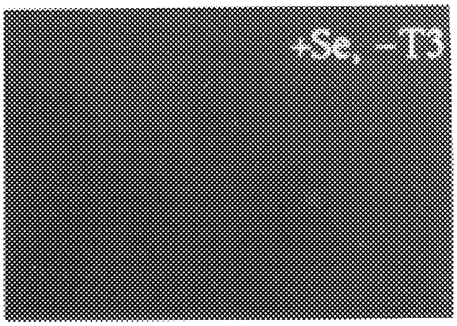
Figure 14C:
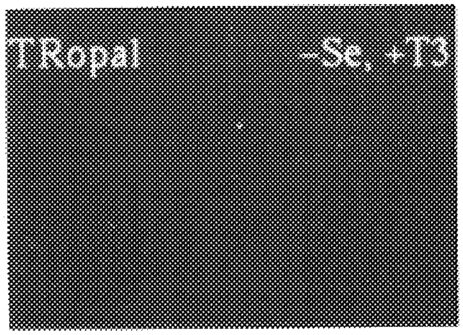
Figure 14D:
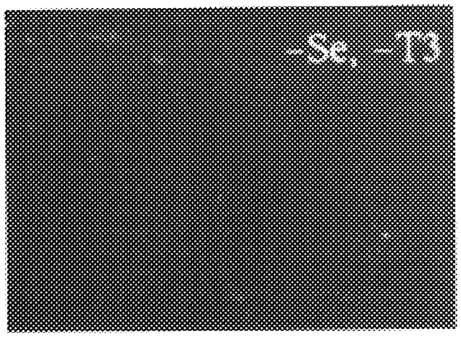
Figure 14E:
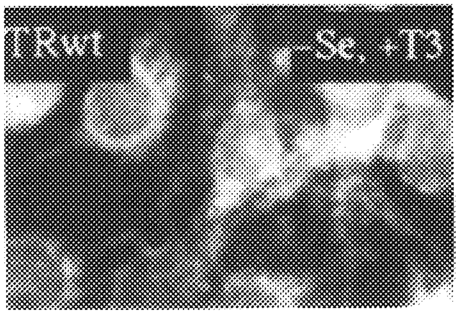
Figure 14F:
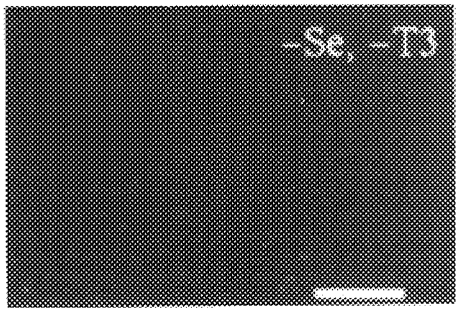

Removal of selenium from the culture conditions led to the complete loss of $T_3$-dependent expression of myelin basic protein in clone 9 cells (FIGS. 14C and D), while the absence of selenium had no effect on $T_3$-dependent expression of this protein in control cells carrying the wild-type TR (FIGS. 14E and F). When 40 nM selenium was added to the culture medium clone 9 cells showed a full $T_3$-dependent expression of myelin basic protein (FIGS. 14A and B). Thus, hormone-dependent expression of the native gene, myelin basic protein, requires both $T_3$ and selenium in clone 9 cells that express the opal mutant of the TR, while changes in selenium availability had no effect on hormone responsiveness of this gene product in cells expressing the wild-type TR.

In these studies, selenium-dependent translation of two target cDNAs was conferred by conservative replacement of selenocysteine for cysteine using mutation of a UGU (encoding cysteine) to a UGA (encoding selenocysteine or termination), then fusion of the mutated coding region to a 3'UTR containing the STE from GPX1, a ubiquitous selenoprotein gene. The resultant opal rGHR.STE and opal hTR.STE constructs demonstrated selenium-dependent expression of each receptor, and the selenoprotein products maintained normal ligand binding and signal transduction capabilities. These findings definitively establish the ability of an STE in the 3'untranslated region of an mRNA to interpret a coding region UGA codon as a signal for selenocysteine incorporation rather than for chain termination, with preservation of function in gene products containing selenocysteine substitutions at selected sites. The system creates the potential for the general application of selenium-dependent translational control to the expression of a wide variety of target genes, and for site-specific heavy atom substitution or $^{75}$Se radioisotopic labeling of the transfected gene products.

Expression of Selenopolypeptides

Polypeptides according to the invention can be produced by the expression of a recombinant nucleic acid having a sequence encoding the polypeptide linked to a recombinant nucleic acid containing a stem-loop structure required for translation of selenocysteine, using any appropriate expression system, e.g., transformation of a suitable eukaryotic host cell with the recombinant nucleic acid in a suitable expression vehicle such as those described above. Those skilled in the field of molecular biology will understand that any of a wide variety of expression systems can be used to provide a selenocysteine-containing recombinant protein of the invention. The precise host cell used is not critical to the invention and can be *Saccharomyces cerevisiae* or any of numerous mammalian cells (e.g., COS-1, HL-60, CV-1, LLC/PK-1, C-6, 3T3L1, and CHO cells). Such cells are available from a wide range of sources (e.g., the American Type Culture collection, Rockland, Md.). The method of transformation or transfection, and the choice of expression vehicle, will depend on the nature of the polypeptide to be expressed and the host system selected. Transformation and transfection methods are described, e.g., in Ausebel et al. (*Current Protocols in Molecular Biology,* John Wiley & Sons, New York, 1989); expression vehicles can be chosen from those well-known in the art, e.g., in *Cloning Vectors: A Laboratory Manual* (P. H. Pouwels et al., 1985, Suppl. 1987).

For example, the cDNA encoding a desired polypeptide can be inserted into either of the eukaryotic expression vectors pcDNA1/neo and pRC/CMV (InVitrogen), which are especially preferred as parent vectors for the selenocysteine expression system of the invention, in an orientation designed to allow expression.

Alternatively, selenocysteine-containing polypeptides according to the invention can be produced by a stably-transfected mammalian cell line. A number of vectors suitable for stable transfection of mammalian cells are available to the public, e.g., see Pouwels et al., supra. Methods for constructing such cell lines are also publicly available, e.g., in Ausebel et al., supra.

Once the desired selenopolypeptide is stably transfected into a host system, the production of the polypeptide is controlled by the content of the selenium in the medium. Selenium deficient cell culture systems have been described (Speirer et al., supra; Chada et al., supra). Normally, the production of a selenocysteine protein will be inhibited at selenium concentrations below 0.1 ng per ml medium, and induced at concentrations above 1 ng per ml. The optimal induction of selenopolypeptide production occurs at approximately 5 to 25 ng per ml medium with concentrations above 50 to 100 ng/ml being cytotoxic, depending on the cell type used.

Once the recombinant polypeptide is expressed, it can be isolated according to methods well known in the art and the functional activity can be determined by assays appropriate for the particular polypeptide, e.g., enzymatic activity or binding affinity. When the desired selenopolypeptide is expressed in cells that contain a native protein with the same functional activities, the selenopolypeptide can be distinguished from the native protein by its higher reactivity with nucleophilic agents due to the selenocysteine moiety as described in Leonard et al., *Biochim. Biophys.* Acta 787:122 (1984), or alternatively by radiolabeling with $^{75}$Se, as described herein.

Expression of Selenopolypeptides In Vivo

The gene for any desired polypeptide which has been modified according to the methods described herein to encode a selenocysteine amino acid residue also can be used to produce a transgenic animal in which production of the polypeptide is controlled by the selenium content in the diet of animal. Methods for producing transgenic animals are well known (e.g., see Hogan et al., *Manipulating the Mouse Embryo: A laboratory manual,* CSH Press, Cold Spring Harbor, N.Y., 1986; Leder et al., U.S. Pat. No. 4,736,866). Typically, expression of the desired selenopolypeptide in a transgenic animal will be inhibited when the animal is given a diet containing less than 0.016 mg/kg selenium, whereas high levels of the protein will be produced when the animal is given a diet containing 0.1 mg/kg or more selenium (e.g., as $Na_2SeO_3$, Sigma).

Other Embodiments

The methods of the invention can also be used to produce high levels of any commercially desirable selenopolypeptide. As discussed above, the presence of available selenium produces a 30 to 50 fold increase in the expression of a selenopolypeptide over the level produced under selenium deficient conditions. This level can be further increased by cotransfecting the cell with a gene encoding the selenocysteine tRNA in an expression vehicle which will allow overexpression of the tRNA under the appropriate conditions, e.g., when selenium is present. For example, this can be accomplished by putting the gene encoding the tRNA under the control of an inducible promoter and then supplying the factor required for induction of the gene at the same time, or before, the medium is supplemented with selenium.

What is claimed is:

1. A method of controlling the production in a eukaryotic cell of a heterologous polypeptide that does not contain selenocysteine in its native form, said method comprising, (1) transfecting a cell with (i) a first nucleic acid encoding said heterologous polypeptide, wherein at least one codon of mRNA transcribed from said first nucleic acid is replaced by the codon UGA, and (ii) a second nucleic acid operably linked to said first nucleic acid, said second nucleic acid directing the translation of said UGA codon as selenocysteine only when said cell can obtain selenium from the medium in which said cell is grown, wherein said second nucleic acid comprises a continuous stretch of at least 79 nucleotides comprising three stem elements, each having a 5' half and a 3' half, and three loop elements, each having a 5' end and a 3' end, wherein the stem elements comprise a) a base stem comprising at least 16 nucleotides that can form 8 complementary pairs of nucleotides, b) a lower stem comprising at least 16 nucleotides that can form 8 complementary pairs of nucleotides, the first nucleotide of the 5' half of the lower stem being bound to the last nucleotide of the 5' half of the base stem, and the first nucleotide of the 3' half of the lower stem being bound to the last nucleotide of the 3' half of the base stem, and c) an upper stem comprising at least 22 nucleotides that can form 11 complementary pairs of nucleotides, wherein the loop elements comprise d) a first loop consisting of 5'-AUGRG-3' (SEQ ID NO:26), the 5'-A being bound to the last nucleotide of the 5' half of the lower stem and the 3'-G being bound to the first nucleotide of the 5' half of the upper stem, e) a second loop consisting of 5'-YRNNNNUAV-3' (SEQ ID NO:27), the 5'-Y being bound to the first nucleotide of the 3' half of the upper stem and the 3'-V being bound to the last nucleotide of the 3' half of the lower stem, and f) a third, apical loop consisting of 5'-ARANNNNNNNN-3' (SEQ ID NO:28), the 5'-A being bound to the last nucleotide of the 5' half of the upper stem and the 3'-N being bound to the last nucleotide of the 3' half of the upper stem, and wherein each A is adenine, G is guanine, N is adenine, guanine, cytosine, or uracil, R is guanine or adenine, U is uracil, V is any nucleotide except thymidine or uracil, and Y is uracil or cytosine; and (2) growing said cell in culture under conditions wherein the production of said polypeptide is controlled by the level of selenium available to said cell.

2. A method of claim 1, wherein said cell is a mammalian cell.

3. A method of claim 1, wherein said cell is a yeast cell.

4. A method of claim 1, wherein said first and second nucleic acids are maintained in said cell in a recombinant vector which autonomously replicates in said cell.

5. A method of claim 1, wherein said first and second nucleic acids are stably integrated into the genome of said cell.

6. A method of claim 1, wherein said second nucleic acid further comprises a first mutually exclusive multiple cloning site tail attached to the first nucleotide of the 5' half of the base stem and a second mutually exclusive multiple cloning site tail attached to the first nucleotide of the 3' half of the base stem.

7. A method of claim 1, wherein said second nucleic acid is synthetic, and comprises a continuous stretch of 87 nucleotides, wherein a) nucleotides 1 to 8 are complementary to nucleotides 87 to 80, respectively, and when base-paired together form a base stem consisting of 16 nucleotides in 8 complementary pairs of nucleotides, b) nucleotides 9 to 20 and 69 to 79 when base-paired together form a lower stem consisting of at least 8 complementary pairs of nucleotides, c) nucleotides 21 to 25 are 5'-$A_{21}U_{22}G_{23}R_{24}G_{25}$-3' (SEQ ID NO:26) and form a first loop, d) nucleotides 60 to 68 are 5'-$Y_{60}R_{61}N_{62}N_{63}N_{64}N_{65}U_{66}A_{67}V_{68}$-3' (SEQ ID NO:27) and form a second loop, e) nucleotides 26 to 37 and nucleotides 49 to 59 when base-paired together form an upper stem of at least 11 complementary pairs of nucleotides, and f) nucleotides 38–48 are non-complementary and are 5'-$A_{38}R_{39}A_{40}N_{41}N_{42}N_{43}N_{44}N_{45}N_{46}N_{47}N_{48}$-3' (SEQ ID NO:28) and from a third, apical loop, and wherein A is adenine, G is guanine, N is adenine, guanine, cytosine, or uracil, R is guanine or adenine, U is uracil, V is any nucleotide except thymidine or uracil, and Y is uracil or cytosine.

8. A method of claim 1, wherein said polypeptide is produced by said cell when the concentration of selenium is 1 to 25 ng per milliliter of growth medium.

9. A method of claim 1, wherein said cell does not comprise a native protein identical to said heterologous polypeptide.

10. A method of claim 1, wherein said cell contains a native protein that is at least 90% identical to said heterologous polypeptide and said heterologous polypeptide is distinguished from said native protein by the increased reactivity of said heterologous polypeptide to a nucleophilic reagent.

11. A method of claim 1, wherein said cell contains a native protein that is at least 90% identical to said heterologous polypeptide and said heterologous polypeptide is distinguished from said native protein by the ability of said heterologous polypeptide, but not said native protein, to incorporate the radioisotope $^{75}Se$.

12. A synthetic single-stranded nucleic acid capable of forming a stem-loop secondary structure, comprising a continuous stretch of at least 79 nucleotides comprising three stem elements, each having a 5' half and a 3' half, and three loop elements, each having a 5' end and a 3' end, wherein the stem elements comprise a) a base stem comprising at least 16 nucleotides which form 8 complementary pairs of nucleotides, b) a lower stem comprising at least 16 nucleotides which form 8 complementary pairs of nucleotides, the first nucleotide of the 5' half of the lower stem being bound to the last nucleotide of the 5' half of the base stem, and the first nucleotide of the 3' half of the lower stem being bound to the last nucleotide of the 3' half of the base stem, and c) an upper stem comprising at least 22 nucleotides which form 11 complementary pairs of nucleotides, wherein the loop elements comprise d) a first loop consisting of 5'-AUGRG-3' (SEQ ID NO:26), the 5'-A being bound to the last nucleotide of the 5' half of the lower stem and the 3'-G being bound to the first nucleotide of the 5' half of the upper stem, e) a second loop consisting of 5'-YRNNNNUAV-3' (SEQ ID NO:27), the 5'-Y being bound to the first nucleotide of the 3' half of the upper stem and the 3'-V being bound to the last nucleotide of the 3' half of the lower stem, and f) a third, apical loop consisting of 5'-ARANNNNNNNN-3' (SEQ ID NO:28), the 5'-A being bound to the last nucleotide of the 5' half of the upper stem and the 3'-N being bound to the last nucleotide of the 3' half of the upper stem, and wherein each A is adenine, G is guanine, N is adenine, guanine, cytosine, or uracil, R is guanine or adenine, U is uracil, V is any nucleotide except thymidine or uracil, and Y is uracil or cytosine.

13. A synthetic single-stranded nucleic acid of claim 12, wherein a) nucleotides 1 to 8 are complementary to nucleotides 87 to 80, respectively, and when base-paired together form a base stem consisting of 16 nucleotides in 8 complementary pairs of nucleotides, b) nucleotides 9 to 20 and 69 to 79 when base-paired together form a lower stem consisting of at least 8 complementary pairs of nucleotides, c) nucleotides 21 to 25 are 5'-$A_{21}U_{22}G_{23}R_{24}G_{25}$-3' (SEQ ID NO:26) and form a first loop, d) nucleotides 60 to 68 are 5'-$Y_{60}R_{61}N_{62}N_{63}N_{64}N_{65}U_{66}A_{67}V_{68}$-3' (SEQ ID NO:27) and form a second loop, e) nucleotides 26 to 37 and nucleotides 49 to 59 when base-paired together form an upper stem of at least 11 complementary pairs of nucleotides, and f) nucleotides 38–48 are non-complementary and are 5'-$A_{38}R_{39}A_{40}N_{41}N_{42}N_{43}N_{44}N_{45}N_{46}N_{47}N_{48}$-3' (SEQ ID NO:28) and form a third, apical loop, and wherein A is adenine, G is guanine, N is adenine, guanine, cytosine, or uracil, R is guanine or adenine, U is uracil, V is any nucleotide except thymidine or uracil, and Y is uracil or cytosine.

14. An isolated double-stranded nucleic acid comprising DNA encoding the single-stranded nucleic acid of claim 12.

15. An isolated nucleic acid having the sequence of FIG. 9E (SEQ ID NO:1).

16. An isolated nucleic acid having the sequence of FIG. 9F (SEQ ID NO:2).

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:1:

NNNNNNNNNN NNNNNNNNNN AUGRGNNNNN NNNNNNNARA NNNNNNNNNN NNNNNNNNNY 60

RNNNNUAVNN NNNNNNNNNN NNNNNNN 87

( 2 ) INFORMATION FOR SEQ ID NO:2:

( i ) SEQUENCE CHARACTERISTICS:
( A ) LENGTH: 86 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:2:

AGAGCUCCAC CAUAAAAGAA UGAGCCACAA GGAGGAAACC UACGAGUCUC CUUUGUGGUG 60

AUCUUACUCU ACUUUGGGGG GGCUCU 86

( 2 ) INFORMATION FOR SEQ ID NO:3:

( i ) SEQUENCE CHARACTERISTICS:
( A ) LENGTH: 832 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

GCGCC 5

ATG TGT GCT GCT CGG CTA GCG GCG GCG GCG GCC CAG TCG GTG TAT GCC 53
Met Cys Ala Ala Arg Leu Ala Ala Ala Ala Ala Gln Ser Val Tyr Ala
1 5 10 15

TTC TCG GCG CGC CCG CTG GCC GGC GGG GAG CCT GTG AGC CTG GGC TCC 101
Phe Ser Ala Arg Pro Leu Ala Gly Gly Glu Pro Val Ser Leu Gly Ser
20 25 30

CTG CGG GGC AAG GTA CTA CTT ATC GAG AAT GTG GCG TCC CTC TGA GGC 149
Leu Arg Gly Lys Val Leu Leu Ile Glu Asn Val Ala Ser Leu SeC Gly
35 40 45

ACC ACG GTC CGG GAC TAC ACC CAG ATG AAC GAG CTG CAG CGG CGC CTC 197
Thr Thr Val Arg Asp Tyr Thr Gln Met Asn Glu Leu Gln Arg Arg Leu
50 55 60

GGA CCC CGG GGC CTG GTG GTG CTC GGC TTC CCG TGC AAC CAG TTT GGG 245
Gly Pro Arg Gly Leu Val Val Leu Gly Phe Pro Cys Asn Gln Phe Gly
65 70 75 80

CAT CAG GAG AAC GCC AAG AAC GAA GAG ATT CAG AAT TCC CTC AAG TAC 293
His Gln Glu Asn Ala Lys Asn Glu Glu Ile Gln Asn Ser Leu Lys Tyr
85 90 95

-continued

```
GTC CGG CCT GGT GGT GGG TTC GAG CCC AAC TTC ATG CTC TTC GAG AAG     341
Val Arg Pro Gly Gly Gly Phe Glu Pro Asn Phe Met Leu Phe Glu Lys
            100                 105                 110

TGC GAG GTG AAC GGT GCG GGG GCG CAC CCT CTC TTC GCC TTC CTG CGG     389
Cys Glu Val Asn Gly Ala Gly Ala His Pro Leu Phe Ala Phe Leu Arg
        115                 120                 125

GAG GCC CTG CCA GCT CCC AGC GAC GAC GCC ACC GCG CTT ATG ACC GAC     437
Glu Ala Leu Pro Ala Pro Ser Asp Asp Ala Thr Ala Leu Met Thr Asp
    130                 135                 140

CCC AAG CTC ATC ACC TGG TCT CCG GTG TGT CGC AAC GAT GTT GCC TGG     485
Pro Lys Leu Ile Thr Trp Ser Pro Val Cys Arg Asn Asp Val Ala Trp
145                 150                 155                 160

AAC TTT GAG AAG TTC CTG GTG GGC CCT GAC GGT GTG CCC CTA CGC AGG     533
Asn Phe Glu Lys Phe Leu Val Gly Pro Asp Gly Val Pro Leu Arg Arg
                165                 170                 175

TAC AGC CGC CGC TTC CAG ACC ATT GAC ATC GAG CCT GAC ATC GAA GCC     581
Tyr Ser Arg Arg Phe Gln Thr Ile Asp Ile Glu Pro Asp Ile Glu Ala
            180                 185                 190

CTG CTG TCT CAA GGG CCC AGC TGT GCC TAG                             611
Leu Leu Ser Gln Gly Pro Ser Cys Ala AM
        195                 200

GGCGCCCCTC CTACCCCGGC TGCTTGGCAG TTGCAGTGCT GCTGTCTCGG GGGGGTTTTC   671

ATCTATGAGG GTGTTTCCTC TAAACCTACG AGGGAGGAAC ACCTGATCTT ACAGAAAATA   731

CCACCTCGAG ATGGGTGCTG GTCCTGTTGA TCCCAGTCTC TGCCAGACCA AGGCGAGTTT   791

CCCCACTAAT AAAGTGCCGG GTGTCAGCAA AAAAAAAAAA A                       832
```

( 2 ) INFORMATION FOR SEQ ID NO: 4:

( i ) SEQUENCE CHARACTERISTICS:
( A ) LENGTH: 18
( B ) TYPE: nucleic acid
( C ) STRANDEDNESS: single
( D ) TOPOLOGY: linear ( x i ) SEQUENCE DESCRIPTION: SEQ ID NO: 4:

```
GGAAACAGCT ATGACCAT     18
```

( 2 ) INFORMATION FOR SEQ ID NO: 5:

( i ) SEQUENCE CHARACTERISTICS:
( A ) LENGTH: 18
( B ) TYPE: nucleic acid
( C ) STRANDEDNESS: single
( D ) TOPOLOGY: linear ( x i ) SEQUENCE DESCRIPTION: SEQ ID NO: 5:

```
GTAAAACGAC GGCCAGTG     18
```

( 2 ) INFORMATION FOR SEQ ID NO: 6:

( i ) SEQUENCE CHARACTERISTICS:
( A ) LENGTH: 36
( B ) TYPE: nucleic acid
( C ) STRANDEDNESS: single
( D ) TOPOLOGY: linear ( x i ) SEQUENCE DESCRIPTION: SEQ ID NO: 6:

```
AATGTGGCGT CCCTCTGAGA CTACACCCAG ATGAAC     36
```

( 2 ) INFORMATION FOR SEQ ID NO: 7:

( i ) SEQUENCE CHARACTERISTICS:
( A ) LENGTH: 36

-continued ( B ) TYPE: nucleic acid
( C ) STRANDEDNESS: single
( D ) TOPOLOGY: linear ( x i ) SEQUENCE DESCRIPTION: SEQ ID NO: 7:

TTACACCGCA GGGAGACTCT GATGTGGGTC TACTTG 36

( 2 ) INFORMATION FOR SEQ ID NO: 8:

( i ) SEQUENCE CHARACTERISTICS:
( A ) LENGTH: 36
( B ) TYPE: nucleic acid
( C ) STRANDEDNESS: single
( D ) TOPOLOGY: linear ( x i ) SEQUENCE DESCRIPTION: SEQ ID NO: 8:

AACGAGCTGC AGCGGCGCCT GGTGGTGCTC GGCTTC 36

( 2 ) INFORMATION FOR SEQ ID NO: 9:

( i ) SEQUENCE CHARACTERISTICS:
( A ) LENGTH: 36
( B ) TYPE: nucleic acid
( C ) STRANDEDNESS: single
( D ) TOPOLOGY: linear ( x i ) SEQUENCE DESCRIPTION: SEQ ID NO: 9:

TTGCTCGACG TCGCCGCGGA CCACCACGAG CCGAAG 36

( 2 ) INFORMATION FOR SEQ ID NO: 10:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 10:

TGAGGCACCA CGGTCCGGCG CCTCGGACCC CGG 33

( 2 ) INFORMATION FOR SEQ ID NO: 11:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 11:

ACTCCGTGGT GCCAGGCCGC GGAGCCTGGG GCC 33

( 2 ) INFORMATION FOR SEQ ID NO: 12:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 12:

CTCGGACCCC GGGGCCTGTT CCCGTGCAAC CAG 33

( 2 ) INFORMATION FOR SEQ ID NO: 13:

( i ) SEQUENCE CHARACTERISTICS:
( A ) LENGTH: 33
( B ) TYPE: nucleic acid
( C ) STRANDEDNESS: single ( D ) TOPOLOGY: linear ( x i ) SEQUENCE DESCRIPTION: SEQ ID NO: 13:

GAGCCTGGGG CCCCGGACAA GGGCACGTTG GTC 33

( 2 ) INFORMATION FOR SEQ ID NO: 14:

( i ) SEQUENCE CHARACTERISTICS:
( A ) LENGTH: 36
( B ) TYPE: nucleic acid
( C ) STRANDEDNESS: single
( D ) TOPOLOGY: linear ( x i ) SEQUENCE DESCRIPTION: SEQ ID NO: 14:

ATCGAGAATG TGGCGTCCTG AGGCACCACG GTCCGG 36

( 2 ) INFORMATION FOR SEQ ID NO: 15:

( i ) SEQUENCE CHARACTERISTICS:
( A ) LENGTH: 36
( B ) TYPE: nucleic acid
( C ) STRANDEDNESS: single
( D ) TOPOLOGY: linear ( x i ) SEQUENCE DESCRIPTION: SEQ ID NO: 15:

TAGCTCTTAC ACCGCAGGAC TCCGTGGTGC CAGGCC 36

( 2 ) INFORMATION FOR SEQ ID NO: 16:

( i ) SEQUENCE CHARACTERISTICS:
( A ) LENGTH: 32
( B ) TYPE: nucleic acid
( C ) STRANDEDNESS: single
( D ) TOPOLOGY: linear ( x i ) SEQUENCE DESCRIPTION: SEQ ID NO: 16:

ATGAGGGTGT TTCCTCCCTA CGAGGGAGGA AC 32

( 2 ) INFORMATION FOR SEQ ID NO: 17:

( i ) SEQUENCE CHARACTERISTICS:
( A ) LENGTH: 32
( B ) TYPE: nucleic acid
( C ) STRANDEDNESS: single
( D ) TOPOLOGY: linear ( x i ) SEQUENCE DESCRIPTION: SEQ ID NO: 17:

TACTCCCACA AAGGAGGGAT GCTCCCTCCT TG 32

( 2 ) INFORMATION FOR SEQ ID NO: 18:

( i ) SEQUENCE CHARACTERISTICS:
( A ) LENGTH: 32
( B ) TYPE: nucleic acid
( C ) STRANDEDNESS: single
( D ) TOPOLOGY: linear ( x i ) SEQUENCE DESCRIPTION: SEQ ID NO: 18:

ACGAGGGAGG AACACCCTTA CAGAAAATAC CA 32

( 2 ) INFORMATION FOR SEQ ID NO: 19:

( i ) SEQUENCE CHARACTERISTICS:
( A ) LENGTH: 32
( B ) TYPE: nucleic acid
( C ) STRANDEDNESS: single
( D ) TOPOLOGY: linear -continued ( x i ) SEQUENCE DESCRIPTION: SEQ ID NO: 19:

TGCTCCCTCC TTGTGGGAAT GTCTTTTATG GT 32

( 2 ) INFORMATION FOR SEQ ID NO: 20:

( i ) SEQUENCE CHARACTERISTICS:
( A ) LENGTH: 43
( B ) TYPE: nucleic acid
( C ) STRANDEDNESS: single
( D ) TOPOLOGY: linear ( x i ) SEQUENCE DESCRIPTION: SEQ ID NO: 20:

CGATAGCGCC ATGTACCCAT ACGACGTCCC AGACTACGCT CGG 43

( 2 ) INFORMATION FOR SEQ ID NO: 21:

( i ) SEQUENCE CHARACTERISTICS:
( A ) LENGTH: 45
( B ) TYPE: nucleic acid
( C ) STRANDEDNESS: single
( D ) TOPOLOGY: linear ( x i ) SEQUENCE DESCRIPTION: SEQ ID NO: 21:

CTAGCCGAGC GTAGTCTGGG ACGTCGTATG GGTACATGGC GCTAT 45

( 2 ) INFORMATION FOR SEQ ID NO: 22:

( i ) SEQUENCE CHARACTERISTICS:
( A ) LENGTH: 30
( B ) TYPE: nucleic acid
( C ) STRANDEDNESS: single
( D ) TOPOLOGY: linear ( x i ) SEQUENCE DESCRIPTION: SEQ ID NO: 22:

ATATATCGAT ATGACTAGCA GAAGCACAGC 30

( 2 ) INFORMATION FOR SEQ ID NO: 23:

( i ) SEQUENCE CHARACTERISTICS:
( A ) LENGTH: 37
( B ) TYPE: nucleic acid
( C ) STRANDEDNESS: single
( D ) TOPOLOGY: linear ( x i ) SEQUENCE DESCRIPTION: SEQ ID NO: 23:

ATATATCCTA GGCACAGTTG CTACAACACT GGCTCTT 37

( 2 ) INFORMATION FOR SEQ ID NO: 24:

( i ) SEQUENCE CHARACTERISTICS:
( A ) LENGTH: 39
( B ) TYPE: nucleic acid
( C ) STRANDEDNESS: single
( D ) TOPOLOGY: linear ( x i ) SEQUENCE DESCRIPTION: SEQ ID NO: 24:

TTCCTCACCC AGTCCGTTTG ACTAGATGAC ACAACAGTG 39

( 2 ) INFORMATION FOR SEQ ID NO: 25:

( i ) SEQUENCE CHARACTERISTICS:
( A ) LENGTH: 39
( B ) TYPE: nucleic acid
( C ) STRANDEDNESS: single
( D ) TOPOLOGY: linear ( x i ) SEQUENCE DESCRIPTION: SEQ ID NO: 25:

-continued

AAGGAGTGGG TCAGGCAAAC TGATCTACTG TGTTGTCAC 39

( 2 ) INFORMATION FOR SEQ ID NO:26:

( i ) SEQUENCE CHARACTERISTICS:
( A ) LENGTH: 5 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:26:

AUGRG 5

( 2 ) INFORMATION FOR SEQ ID NO:27:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:27:

YRNNNNUAV 9

( 2 ) INFORMATION FOR SEQ ID NO:28:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:28:

ARANNNNNNN N 11

( 2 ) INFORMATION FOR SEQ ID NO:29:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:29:

CCTAGGAAGA GCTCCACCAT AAAAGAATGA GCCACAAGGA GGAAACCTAC 50

( 2 ) INFORMATION FOR SEQ ID NO:30:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:30:

GAGTCTCCTT TGTGGTGATC TTACTCTACT TTTGGGGGGG CTCTTCTAGA C 51

( 2 ) INFORMATION FOR SEQ ID NO:31:

-continued ( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:31:

TCGAGTCTAG AAGAGCCCCC CCAAAAGTAG AGTAAGATCA CCACA 45

( 2 ) INFORMATION FOR SEQ ID NO:32:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:32:

AAGGAGACTC GTAGGTTTCC TCCTTGTGGC TCATTCTTTT ATGGTGGAGC TCTTCCTAGG 60

( 2 ) INFORMATION FOR SEQ ID NO:33:

( i ) SEQUENCE CHARACTERISTICS:
( A ) LENGTH: 87 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:33:

UCUCGGGGGG GUUUUCAUCU AUGAGGGUGU UUCCUCUAAA CCUACGAGGG AGGAACACCU 60

GAUCUUACAG AAAAUACCAC CUCGAGA 87